(12) United States Patent
Siegel et al.

(10) Patent No.: US 11,291,544 B2
(45) Date of Patent: Apr. 5, 2022

(54) DELIVERY PLATFORMS, DEVICES, AND METHODS FOR TRICUSPID VALVE REPAIR

(71) Applicant: Cedars-Sinai Medical Center, Los Angeles, CA (US)

(72) Inventors: Robert James Siegel, Beverly Hills, CA (US); Richard Cheng, Los Angeles, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 0 days.

(21) Appl. No.: 16/964,922

(22) PCT Filed: Jan. 31, 2019

(86) PCT No.: PCT/US2019/015971
§ 371 (c)(1),
(2) Date: Jul. 24, 2020

(87) PCT Pub. No.: WO2019/152598
PCT Pub. Date: Aug. 8, 2019

(65) Prior Publication Data
US 2020/0375730 A1 Dec. 3, 2020

Related U.S. Application Data

(60) Provisional application No. 62/625,699, filed on Feb. 2, 2018.

(51) Int. Cl.
*A61F 2/24* (2006.01)
*A61B 17/04* (2006.01)
(Continued)

(52) U.S. Cl.
CPC .......... *A61F 2/246* (2013.01); *A61B 17/0469* (2013.01); *A61B 17/12122* (2013.01);
(Continued)

(58) Field of Classification Search
CPC ...... A61F 2/246; A61F 2/2476; A61F 2/2466; A61B 17/0469; A61B 17/12122;
(Continued)

(56) References Cited

U.S. PATENT DOCUMENTS 4,777,951 A   10/1988  Cribier et al.
5,171,259 A   12/1992  Inoue
(Continued)

FOREIGN PATENT DOCUMENTS

CN    106175986    12/2016
EP    1 674 040    6/2006
(Continued)

OTHER PUBLICATIONS

Bhargava et al., "Biosense Left Ventricular Electromechanical Mapping", Asian Cardiovasc Thorac Ann 1999, 7:345-52.
(Continued)

*Primary Examiner* — Jing Rui Ou
(74) *Attorney, Agent, or Firm* — Knobbe, Martens, Olson & Bear LLP

(57) ABSTRACT

Devices and methods for treating tricuspid regurgitation (TR) are provided. A clasp or clamp is used to anchor a TR-treatment device to an existing lead of a pacemaker or an implantable cardioverter defibrillator (ICD) that passes through the tricuspid valve. The TR-treatment device can be a balloon occluder that is adjustable by filling or withdrawing filler material from the occluder through a proximal port implanted in the skin of the patient.

12 Claims, 22 Drawing Sheets

(51) Int. Cl.
   *A61B 17/12* (2006.01)
   *A61N 1/05* (2006.01)
   *A61M 27/00* (2006.01)

(52) U.S. Cl.
   CPC .......... *A61F 2/2466* (2013.01); *A61F 2/2476* (2020.05); *A61N 1/056* (2013.01); *A61B 17/12136* (2013.01); *A61M 27/002* (2013.01); *A61N 1/057* (2013.01)

(58) Field of Classification Search
   CPC ........... A61B 17/12136; A61M 27/002; A61N 1/056; A61N 1/059; A61N 1/0587
   See application file for complete search history.

(56) References Cited

U.S. PATENT DOCUMENTS

| | | |
|---|---|---|
| 5,201,880 A | 4/1993 | Wright et al. |
| 5,573,540 A | 11/1996 | Yoon |
| 5,575,799 A | 11/1996 | Bolanos et al. |
| 5,609,598 A | 3/1997 | Laufer et al. |
| 5,626,588 A | 5/1997 | Sauer et al. |
| 5,716,367 A | 2/1998 | Koike et al. |
| 6,029,671 A | 2/2000 | Stevens et al. |
| 6,051,014 A | 4/2000 | Jang |
| 6,090,096 A | 7/2000 | St. Goar et al. |
| 6,117,144 A | 9/2000 | Nobles et al. |
| 6,117,145 A | 9/2000 | Wood et al. |
| 6,136,010 A | 10/2000 | Modesitt et al. |
| 6,165,183 A | 12/2000 | Kuehn et al. |
| 6,197,043 B1 | 3/2001 | Davidson |
| 6,206,893 B1 | 3/2001 | Klein et al. |
| 6,269,819 B1 | 8/2001 | Oz et al. |
| 6,287,321 B1 | 9/2001 | Jang |
| 6,312,446 B1 | 11/2001 | Huebsch et al. |
| 6,312,447 B1 | 11/2001 | Grimes |
| 6,325,067 B1 | 12/2001 | Sterman et al. |
| 6,328,757 B1 | 12/2001 | Matheny |
| 6,461,366 B1 | 10/2002 | Seguin |
| 6,508,828 B1 | 1/2003 | Akerfeldt et al. |
| 6,575,971 B2 | 6/2003 | Hauck et al. |
| 6,629,534 B1 | 10/2003 | St. Goar et al. |
| 6,635,068 B1 | 10/2003 | Dubrul et al. |
| 6,752,813 B2 | 6/2004 | Goldfarb et al. |
| 6,770,083 B2 | 8/2004 | Seguin |
| 6,926,715 B1 | 8/2005 | Hauck et al. |
| 6,932,792 B1 | 8/2005 | St. Goar et al. |
| 6,945,978 B1 | 9/2005 | Hyde |
| 7,048,754 B2 | 5/2006 | Martin et al. |
| 7,226,467 B2 | 6/2007 | Lucatero et al. |
| 7,276,078 B2 * | 10/2007 | Spenser ................ A61F 2/2433 623/1.24 |
| 7,404,824 B1 * | 7/2008 | Webler ................ A61B 17/0644 623/2.36 |
| 7,563,267 B2 | 7/2009 | Goldfarb et al. |
| 7,569,062 B1 | 8/2009 | Kuehn et al. |
| 7,604,646 B2 | 10/2009 | Goldfarb et al. |
| 7,632,308 B2 | 12/2009 | Loulmet |
| 7,635,329 B2 | 12/2009 | Goldfarb et al. |
| 7,666,204 B2 | 2/2010 | Thornton et al. |
| 7,704,269 B2 | 4/2010 | St. Goar et al. |
| 7,736,388 B2 | 6/2010 | Goldfarb et al. |
| 7,811,296 B2 | 10/2010 | Goldfarb et al. |
| 7,828,819 B2 | 11/2010 | Webler et al. |
| 7,854,762 B2 | 12/2010 | Speziali et al. |
| 7,938,827 B2 | 5/2011 | Hauck et al. |
| 7,981,123 B2 | 7/2011 | Seguin |
| 8,052,592 B2 | 11/2011 | Goldfarb et al. |
| 8,123,703 B2 | 2/2012 | Martin et al. |
| 8,172,856 B2 | 5/2012 | Eigler et al. |
| 8,216,256 B2 | 7/2012 | Raschdorf, Jr. et al. |
| 8,216,302 B2 | 7/2012 | Wilson et al. |
| 8,303,608 B2 | 11/2012 | Goldfarb et al. |
| 8,323,334 B2 | 12/2012 | Deem et al. |
| 8,382,796 B2 | 2/2013 | Blaeser et al. |
| 8,409,219 B2 | 4/2013 | Kelley et al. |
| 8,409,273 B2 | 4/2013 | Thornton et al. |
| 8,545,551 B2 | 10/2013 | Loulmet |
| 8,568,472 B2 | 10/2013 | Marchand et al. |
| 8,920,463 B2 | 12/2014 | McGukin, Jr. et al. |
| 8,932,325 B2 | 1/2015 | Stanley et al. |
| 8,992,605 B2 | 3/2015 | Zakai et al. |
| 9,023,099 B2 | 5/2015 | Duffy et al. |
| 9,060,858 B2 | 6/2015 | Thornton et al. |
| 9,474,605 B2 | 10/2016 | Rowe et al. |
| 9,498,330 B2 | 11/2016 | Solem |
| 9,763,658 B2 | 9/2017 | Eigler et al. |
| 10,080,657 B2 | 9/2018 | Siegel |
| 10,105,221 B2 | 10/2018 | Siegel |
| 10,499,905 B2 | 12/2019 | Eigler et al. |
| 10,758,241 B1 * | 9/2020 | Lashinski .......... A61B 17/1214 |
| 10,758,265 B2 | 9/2020 | Siegel |
| 10,799,359 B2 | 10/2020 | Siegel et al. |
| 10,898,323 B2 | 1/2021 | Siegel |
| 2001/0005787 A1 | 6/2001 | Oz et al. |
| 2002/0013571 A1 | 1/2002 | Goldfarb et al. |
| 2003/0120340 A1 | 6/2003 | Liska et al. |
| 2004/0044350 A1 | 3/2004 | Martin et al. |
| 2004/0260322 A1 | 12/2004 | Rudko et al. |
| 2005/0033446 A1 | 2/2005 | Deem et al. |
| 2005/0107871 A1 | 5/2005 | Realyvasquez et al. |
| 2005/0143811 A1 | 6/2005 | Realyvasquez |
| 2005/0222489 A1 | 10/2005 | Rahdert et al. |
| 2005/0273135 A1 | 12/2005 | Chanduszko et al. |
| 2006/0004442 A1 * | 1/2006 | Spenser ................ A61F 2/2409 623/2.11 |
| 2006/0020275 A1 | 1/2006 | Goldfarb et al. |
| 2006/0074484 A1 | 4/2006 | Huber |
| 2006/0089671 A1 | 4/2006 | Goldfarb et al. |
| 2006/0229708 A1 | 10/2006 | Powell et al. |
| 2006/0241745 A1 * | 10/2006 | Solem ..................... A61F 2/246 623/2.18 |
| 2006/0293739 A1 | 12/2006 | Vijay |
| 2007/0032850 A1 | 2/2007 | Ruiz et al. |
| 2007/0038293 A1 | 2/2007 | St.Goar et al. |
| 2007/0055303 A1 | 3/2007 | Vidlund et al. |
| 2007/0093890 A1 * | 4/2007 | Eliasen ................... A61F 2/246 623/2.11 |
| 2007/0198082 A1 * | 8/2007 | Kapadia .................. A61F 2/246 623/2.11 |
| 2007/0255273 A1 | 11/2007 | Fernandez et al. |
| 2007/0270943 A1 | 11/2007 | Solem et al. |
| 2007/0293943 A1 * | 12/2007 | Quinn ..................... A61F 2/246 623/2.11 |
| 2009/0048668 A1 | 2/2009 | Wilson et al. |
| 2009/0062836 A1 | 3/2009 | Kurrus |
| 2009/0076600 A1 | 3/2009 | Quinn |
| 2009/0177266 A1 | 7/2009 | Powell et al. |
| 2010/0022823 A1 | 1/2010 | Goldfarb et al. |
| 2010/0217283 A1 | 8/2010 | St.Goar et al. |
| 2010/0298929 A1 * | 11/2010 | Thornton .............. A61F 2/2445 623/2.1 |
| 2011/0029071 A1 | 2/2011 | Zlotnick et al. |
| 2011/0066233 A1 | 3/2011 | Thornton et al. |
| 2011/0106245 A1 | 5/2011 | Miller et al. |
| 2011/0218620 A1 | 9/2011 | Meiri et al. |
| 2011/0224655 A1 | 9/2011 | Asirvatham et al. |
| 2011/0264208 A1 | 10/2011 | Duffy et al. |
| 2011/0313437 A1 | 12/2011 | Yeh |
| 2011/0319989 A1 | 12/2011 | Lane et al. |
| 2012/0010700 A1 | 1/2012 | Spenser |
| 2012/0065464 A1 | 3/2012 | Ellis et al. |
| 2012/0078360 A1 | 3/2012 | Rafiee |
| 2012/0095547 A1 | 4/2012 | Chuter |
| 2012/0116418 A1 | 5/2012 | Belson et al. |
| 2012/0191181 A1 | 7/2012 | Kassab et al. |
| 2012/0245678 A1 | 9/2012 | Solem |
| 2012/0310331 A1 | 12/2012 | Eigler et al. |
| 2012/0310334 A1 | 12/2012 | Dolan |
| 2013/0018414 A1 | 1/2013 | Widimski et al. |
| 2013/0030522 A1 | 1/2013 | Rowe et al. |
| 2013/0197559 A1 | 8/2013 | Hariton et al. |
| 2013/0226288 A1 | 8/2013 | Goldwasser et al. |
| 2013/0253547 A1 | 9/2013 | Goldfarb et al. |

(56) References Cited

U.S. PATENT DOCUMENTS

| | | | |
|---|---|---|---|
| 2013/0261739 A1 | 10/2013 | Kuehn | |
| 2014/0039607 A1 | 2/2014 | Kovach | |
| 2014/0058502 A1 | 2/2014 | Marchand et al. | |
| 2014/0236198 A1 | 8/2014 | Goldfarb et al. | |
| 2014/0277426 A1* | 9/2014 | Dakin | A61F 2/246 623/2.38 |
| 2014/0371789 A1 | 12/2014 | Hariton et al. | |
| 2015/0038988 A1 | 2/2015 | Tegels et al. | |
| 2015/0134057 A1 | 5/2015 | Rourke et al. | |
| 2015/0173765 A1 | 6/2015 | Miller et al. | |
| 2016/0008129 A1 | 1/2016 | Siegel | |
| 2016/0324635 A1 | 11/2016 | Vidlund et al. | |
| 2017/0143478 A1 | 5/2017 | Schwartz et al. | |
| 2017/0174979 A1 | 6/2017 | Sanders | |
| 2017/0216028 A1 | 8/2017 | Khalil | |
| 2017/0245988 A1 | 8/2017 | Siegel et al. | |
| 2017/0325842 A1 | 11/2017 | Siegel et al. | |
| 2018/0193016 A1 | 7/2018 | Eigler et al. | |
| 2018/0289478 A1 | 10/2018 | Quill | |
| 2019/0008638 A1 | 1/2019 | Siegel et al. | |
| 2019/0076246 A1 | 3/2019 | Siegel | |
| 2019/0298516 A1 | 10/2019 | Siegel et al. | |
| 2019/0365529 A1 | 12/2019 | Siegel et al. | |
| 2020/0121454 A1* | 4/2020 | Spence | A61F 2/2457 |
| 2020/0367926 A1 | 11/2020 | Siegel | |
| 2021/0030534 A1 | 2/2021 | Siegel et al. | |

FOREIGN PATENT DOCUMENTS

| | | |
|---|---|---|
| EP | 1 539 015 | 4/2011 |
| EP | 3 269 330 | 1/2018 |
| JP | 2004-530451 | 10/2004 |
| JP | 2004-531337 | 10/2004 |
| WO | WO 00/60995 | 10/2000 |
| WO | WO 01/26557 | 4/2001 |
| WO | WO 01/070116 | 9/2001 |
| WO | WO 02/034167 | 5/2002 |
| WO | WO 03/049619 | 6/2003 |
| WO | WO 2004/012583 | 2/2004 |
| WO | WO 2005/058239 | 6/2005 |
| WO | WO 2007/011994 | 1/2007 |
| WO | WO 2011/116379 | 9/2011 |
| WO | WO 2014/138284 | 9/2014 |
| WO | WO 2014/138482 | 9/2014 |
| WO | WO 2016/040526 | 3/2016 |
| WO | WO 2016/077783 | 5/2016 |
| WO | WO 2017/015632 | 1/2017 |
| WO | WO 2018/140535 | 8/2018 |
| WO | WO 2019/152598 | 8/2019 |

OTHER PUBLICATIONS

Black MD, M., Division of Pediatric Cardiac Surgery, Standford University School of Medicine, California, USA, Minimally Invasive Pediatric Cardiac Surgery, Online Article in 4 pages.

Ethicon Wound Closure Manual—Chapter 6, Research and Development at Ethicon, Inc.—An Ongoing Process of Change and Improvement, Online at www.ethiconinc.com in 4 pages.

Gersak MD, Ph.D., B., "Mitral Valve Repair or Replacement on the Beating Heart", The Heart Surgery Forum #2000-1989, Jun. 8, 2000, pp. 232-237, 2000 Forum Multimedia Publishing, LLC.

Perclose A-T, 6F Suture-Mediated Closure (SMC) System, Instructions for Use disctributed in the U.S. by Abbott laboratories, Inc. 2002, 2006 Abbott Laboratories in 11 pages.

Quealy et al., "Use of Combined Intravascular Ultrasound and PTCA Catheter: Clinical Utility", Chapter 12, pp. 245-250.

International Search Report and Written Opinion issued in PCT Application No. PCT/US2019/015971, dated Apr. 18, 2019 in 14 pages.

International Preliminary Report on Patentability issued in PCT Application No. PCT/US2019/015971, dated Aug. 4, 2020, in 7 pages.

\* cited by examiner

DELIVERY PLATFORMS, DEVICES, AND METHODS FOR TRICUSPID VALVE REPAIR

CROSS-REFERENCE TO RELATED APPLICATIONS

This application is a national stage application under 35 U.S.C. § 371 of International Application No. PCT/US2019/015971, filed on Jan. 31, 2019, which published in English as WO 2019/152598 A2 on Aug. 8, 2019, and which claims priority benefit of U.S. Patent Application No. 62/625,699, filed on Feb. 2, 2018.

BACKGROUND

Technical Field

The present disclosure relates generally to devices and methods for treating regurgitation in a heart valve. Specifically, the present disclosure relates to treating tricuspid regurgitation in a patient having a medical device lead (e.g., an implantable cardioverter defibrillator lead or a pacemaker lead) that passes through the tricuspid valve.

Description of the Related Art

The tricuspid valve separates the right lower heart chamber (the right ventricle) from the right upper heart chamber (right atrium). Tricuspid regurgitation (TR) is a disorder in which the tricuspid valve does not close tight enough, allowing blood to flow backward into the right upper heart chamber (atrium) when the right lower heart chamber (ventricle) contracts. To compensate for TR, the right ventricle enlarges so that it can pump harder, which sometimes causes the tricuspid opening to become stretched out and floppy, worsening the TR. When TR is severe, it may be necessary to repair or replace the valve.

A large proportion of patients with significant TR also have a preexisting pacemaker or implantable cardioverter defibrillator (ICD) lead. The pacemaker lead or ICD lead can pass through the tricuspid valve with a distal end of the lead anchored in a ventricular wall of the heart to provide electrical stimulation thereof. The portion of the lead that passes through the tricuspid valve can interfere with closure of the valve leaflets thereby causing or exacerbating TR.

SUMMARY

For these reasons, there exists a need for minimally invasive methods of treating TR in patients having an existing pacemaker or ICD lead that passes through the tricuspid valve. The present disclosure is directed to occluder devices that can be delivered endovascularly. In some aspects, the present disclosure is directed to a delivery platform that includes a mechanism to engage a preexisting lead (e.g., pacemaker lead or ICD lead), and carry (e.g., in a monorail fashion) a balloon occluder, shunt, umbrella, or other device to the tricuspid valve. The delivery platform can include a mechanism to secure the carried device or devices in place. In some aspects, the occluder devices can be balloons of varying shapes (e.g., cylindrical, cone, asymmetric). The balloon occluder can be filled with biologically-compatible liquids or semi-solid liquids, with or without a communicating chamber tunneled under the skin that can be used to change the size of the balloons as the tricuspid valve annulus remodels with time. The devices can be customizable to each patient. Shunt devices can be deployed at the level of the valve and include one-way valves, seawall-type shunt devices, or other structures. Umbrella-like shunt devices can allow laminar diastolic filling while selectively obstructing TR by the shape of the device itself. Some devices can include moveable parts (e.g., micro-slats) that open with diastolic flow and close shut during systole by the TR jet. In some aspects, the delivery platform can be used for future indications that could utilize the platform to deliver other novel devices, gene therapies, and drugs, to the right atrium, right ventricle, pulmonary arteries, and lungs.

BRIEF DESCRIPTION OF THE DRAWINGS

A more complete appreciation of the subject matter of this application and the various advantages thereof can be realized by reference to the following detailed description, in which reference is made to the accompanying drawings in which.

DETAILED DESCRIPTION

Figure 1:
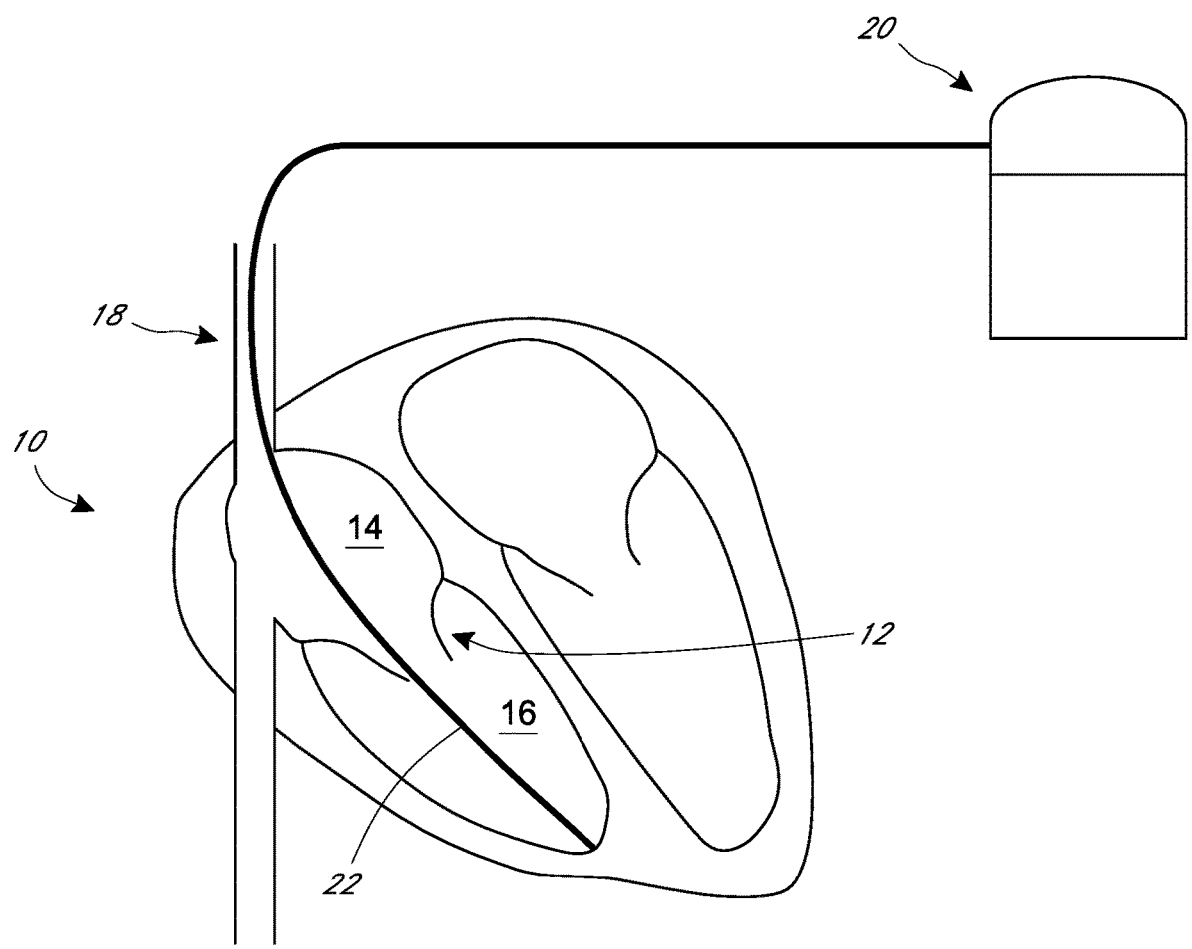
FIG. 1 depicts a cross-sectional view of a heart in normal diastole with an ICD lead passing through the tricuspid valve.

Pathological TR is estimated to occur in over two million people in the US alone, rivaling the prevalence of mitral regurgitation. TR is associated with kidney and liver damage, heart failure symptoms, hospitalizations, and mortality. However, due to high surgical mortality of 2-10% for isolated tricuspid valve repair, the vast majority of cases of TR are poorly managed medically. There is an immense need for percutaneous solutions for treating TR.

Percutaneous devices for TR repair are in their infancy. Existing devices can be difficult to place and can exclude patients with pacemaker or ICD leads. These devices are not customizable to the size of the annulus, or to future remodeling of the annulus.

The Trialign device (Mitralign, Inc., Boston, Mass.) is a percutaneous investigational device based on the Kay bicuspidization procedure that treats TR with annular reduction through tissue plication. The SCOUT feasibility trial implanted the device in 15 patients with 30-day outcomes published in 2017. Three patients had plication detachments at 30-days, and the long-term efficacy and safety of this device is unknown.

The Forma device (Edwards Lifesciences, Irvine, Calif.) is a percutaneous investigational device implanted from a left subclavian venous puncture. A non-customizable occluder device is delivered via catheters across the tricuspid valve and anchored distally with a screw in lead and proximally at the puncture site. The occluder device size cannot be adjusted after delivery and long-term complications after annular remodeling occurs are not known. It can be placed in patients with existing leads, but the occluder device is symmetrical and pushes the existing lead off to the side. There are no asymmetrical options to take into account the existing lead. Results of this device are not published.

The MitraClip (Abbott Vascular, Abbott Park, Ill.) is a percutaneous clip device approved for the mitral valve for organic/primary mitral regurgitation in high-risk or non-operable patients. It has been used off label to clip TR but long-term outcomes are not known. It is unclear if it is feasible to clip the tricuspid valve in the presence of existing leads.

Patients with heart failure often have concomitant atrial fibrillation, a strong predictor of TR, and pulmonary hypertension from left-sided disease leading to high pressure TR. Pacemakers and ICDs are often implanted in patients with heart failure, atrial fibrillation, and dilated cardiomyopathy, conditions which are commonly associated with TR. A large proportion of patients with significant TR also have preexisting pacemaker or ICD leads. The reasons are multifactorial. First, the leads themselves can erode into the tricuspid leaflet or impinge the leaflets causing geometric distortion and regurgitation. Right ventricular pacing can cause a left bundle and geometric distortion of the annulus causing TR. Finally, patients with heart failure are more likely to both have TR (functional and secondary to the cardiomyopathy) as well as an indication for defibrillator placement.

While the incidence of rheumatic TR has plateaued, the widespread use of pacemakers and ICUs has led to a dramatic increase in pacemaker- or defibrillator-associated TR. The present disclosure addresses multiple issues for this pacemaker- or defibrillator-associated-TR patient cohort. In some aspects, the devices and methods of the present disclosure are designed for this cohort that has a high incidence of tricuspid disease. As discussed in more detail below, the devices and methods of the present disclosure can take into account pre-existing pacemaker or defibrillator leads (e.g., delivery platform design, asymmetric balloon system), as well as can be customized during the procedure to regurgitant reduction, and afterwards (e.g., months to years later). The devices and methods of the present disclosure can address annular remodeling (e.g., may allow increasing of the size of occluder device to address annulus dilatation or worsening cardiomyopathy, or may allow decreasing in size of occluder device to address improvement in TR with treatment). In some aspects, the devices and methods of the present disclosure can be applied to patients without preexisting pacemaker or defibrillator leads (e.g., the balloon occluder devices and shunt devices can be placed onto existing screw-in leads and delivered similarly). The devices and methods can use an anchoring assembly to position a TR treatment device along an existing lead. The anchoring assembly can have a tracking configuration and a secured configuration. The anchoring assembly can move along the lead (e.g., in monorail fashion) when the anchoring assembly is in its tracking configuration. The anchoring assembly can be prevented or inhibited from moving along the lead when the anchoring assembly is in its secured configuration. As discussed in more detail below, the TR treatment device can be attached to the anchoring assembly before or after the anchoring assembly has been placed in the secured configuration that fixes the anchoring assembly onto the lead.

As discussed above, patients with significant TR can also have preexisting pacemaker or ICD leads, which can exacerbate poor coaptation of valve leaflets. FIG. 1 is a schematic representation of a heart 10 in normal diastole. The heart 10 consists of four chambers with the tricuspid valve 12 located between the right atrium 14 and the right ventricle 16. A medical device such as a pacemaker or an ICD 20 can have a lead 22 that extends from the pacemaker or ICD 20 and has a distal portion of the lead 22 embedded into tissue of the heart 10. In the illustrated arrangement of FIG. 1, the lead 22 enters the right atrium 14 from the superior vena cava 18, passes through the tricuspid valve 12, and anchors into a wall of the right ventricle 16.

In systole of the normal-functioning heart, the leaflets of the tricuspid valve 12 meet to seal the right atrium 14 from the right ventricle 16, thereby blocking blood flow from the right ventricle 16 into the right atrium 14 and directing blood to exit the right ventricle 16 through the pulmonary valve (not shown). As discussed above, in systole of a heart exhibiting TR, the leaflets of the tricuspid valve 12 do not completely seal the right atrium 14 from the right ventricle 16, thereby allowing blood to flow from the right ventricle 16 into the right atrium 14 during contraction of the right ventricle 16. A lead 22 (e.g., a pacemaker lead or an ICD lead) that passes through the tricuspid valve 12 can interfere with the movement of the valve leaflets, thereby causing or worsening TR.

Figure 2:
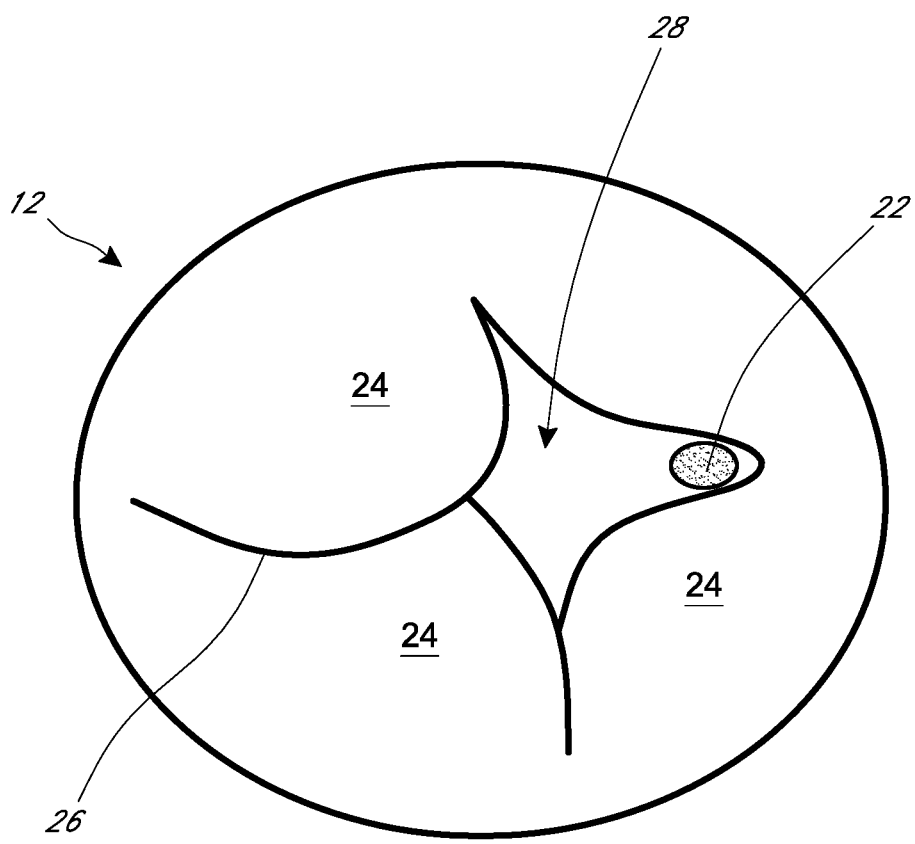
FIG. 2 depicts a top (atrial) view of a tricuspid valve with an medical device lead passing through the tricuspid valve.

FIG. 2 is a schematic representation of a top (or atrial) view of a tricuspid valve 12 that has a lead 22 passing through the tricuspid valve 12. As shown in FIG. 2, the tricuspid valve 12 has three leaflets 24. In the normal-functioning tricuspid valve, the leaflets 24 can meet along a line of coaptation 26 to form a substantially fluid-tight seal. In this way, the normal-functioning tricuspid valve can operate as a one-way valve, allowing flow in the antegrade direction (from the right atrium to the right ventricle) and preventing flow in the retrograde direction (from the right ventricle to the right atrium). As shown in FIG. 2, a lead 22 that passes through the tricuspid valve 12 can interfere with a leaflet 24. The lead 22 can prevent or hinder the leaflet 24 from forming a complete line of coaptation 26 with one or more of the other leaflets 24. A gap 28 can remain between the leaflets 24 during systole, causing or exacerbating TR.

Figure 3:
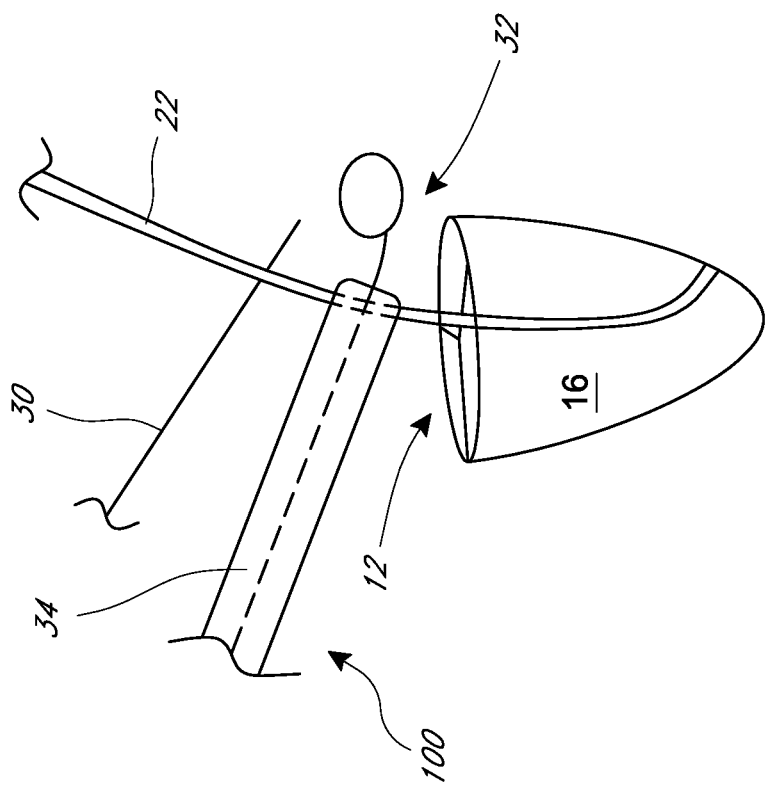
FIG. 3 depicts an embodiment of a delivery device of the present disclosure with a snare and a wire disposed on either side of a pre-existing medical device lead.

FIG. 3 illustrates an embodiment of a delivery platform 100 that uses a wire 30 to deliver a device to the tricuspid valve 12. As shown in FIG. 3, a distal end of the wire 30 can be extended past a first side of an existing pacemaker or ICD lead 22. The existing lead 22 passes through the tricuspid valve 22, and a distal end of the lead 22 is anchored in a wall of the right ventricle 16. A snare 32 can be extended across an opposing side of the lead 22 such that the lead 22 is disposed between the wire 30 and the snare 32.

Figure 4:
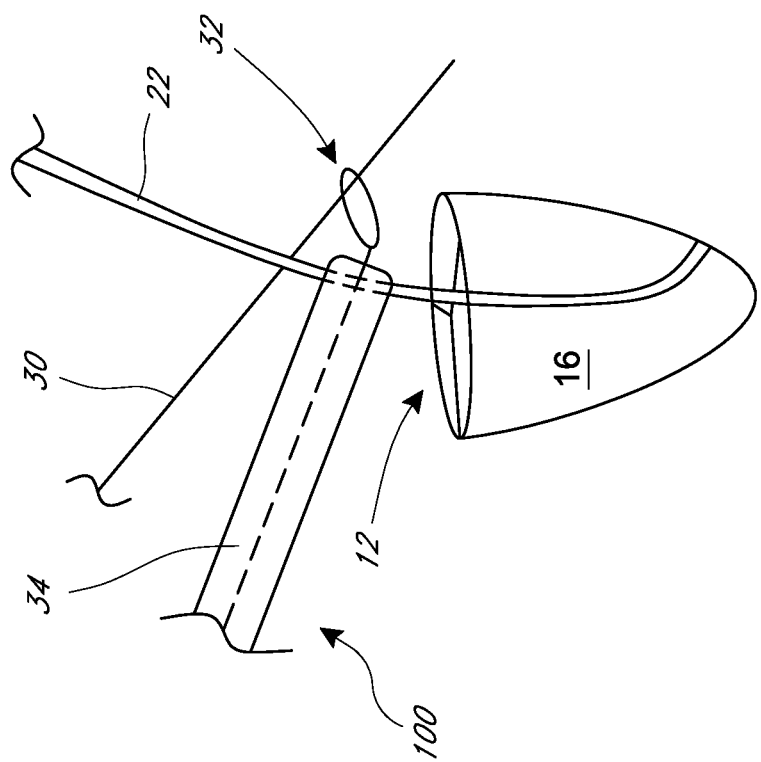
FIG. 4 depicts the embodiment of the delivery device of FIG. 3 with the distal end of the wire passing through the snare.

Referring to FIG. 4, the distal end of the wire 30 can be captured by the snare 32. In the illustrated embodiment, the snare 32 is extended from a catheter 34 and has a lasso-shaped distal end. The wire 30 is passed through the hoop of the lasso-shaped distal end of the snare 32. The snare 32 can be withdrawn into the catheter 34 to secure the distal end of the wire 30 in the snare 32. The delivery platform 100 can use other methods to capture the wire 30. For example, the snare 32 can be hook-shaped and can secure the wire 30 by hooking over a portion of the wire 30 and pulling snare 32 into the catheter 34 to secure the hooked portion of the wire 30 within the catheter 34.

Figure 5:
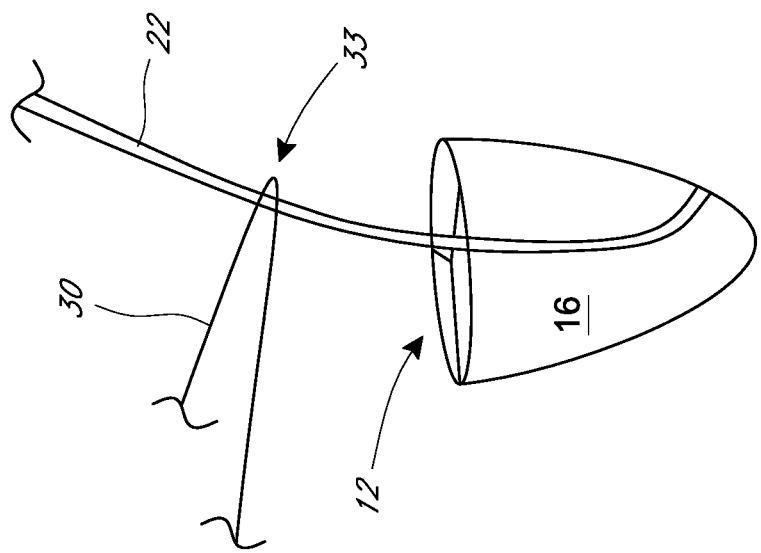
FIG. 5 depicts the wire of FIG. 4 after the distal end of the wire has been drawn around the medical device lead.

After the wire 30 is passed through the hoop of the lasso-shaped snare 32, the snare 32 can be retracted into the catheter 34 to draw the wire 30 into the catheter 34. The distal end of the snare 32 can be withdrawn from the patient, thereby externalizing the distal end of the wire 30. FIG. 5 shows the wire 30 after the distal end of the wire 30 has been externalized. As shown in FIG. 5, the wire 30 forms a bend 33 around the lead 22. After completing the snaring and externalizing of the distal end of the wire 30, the wire 30 forms a bend around the existing lead 22 with the opposing ends of the wire 30 externalized from the patient.

Figure 6:
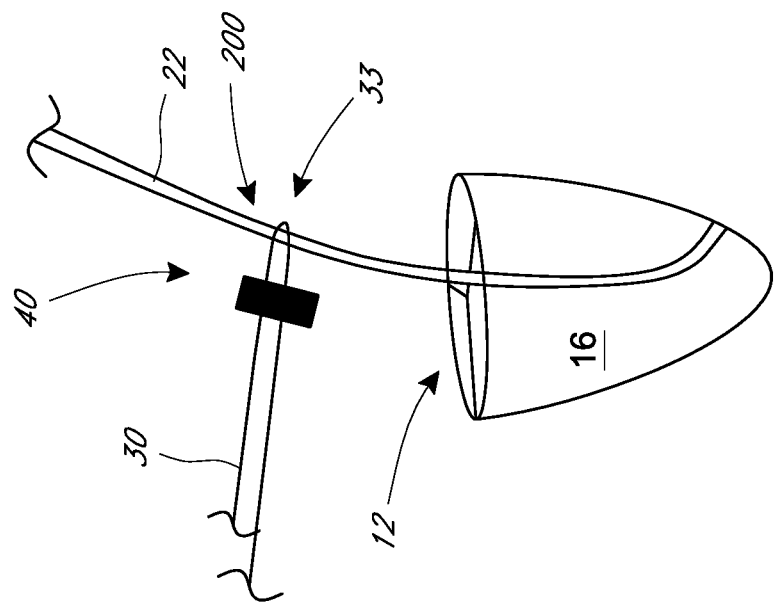
FIG. 6 depicts the wire of FIG. 5 with an anchoring clasp advanced over the wire.

FIG. 6 shows that a clasp 40 can be advanced over the wire 30 to secure the lead 22 within the bend 33 of the wire 30. In the illustrated embodiment, the opposing ends of the wire 30 are passed through clasp 40. The clasp 40 is then advanced over the wire 30 toward the bend 33. As described in more detail below, the clasp 40 and the wire 30 can form an embodiment of an anchoring assembly 200 that allows proper positioning of a TR-treatment device 50 (shown in FIG. 7) along the lead 22. The anchoring assembly 200 can have a tracking configuration and a secured configuration. The anchoring assembly 200 can move or track along the pacemaker or ICD lead 22 when the anchoring assembly 200 is in the tracking configuration. The anchoring assembly 200 can be fixed onto the lead 22 when the anchoring assembly 200 is in the secured configuration, thereby preventing or inhibiting movement of the anchoring assembly 200 along the lead 22.

With continued reference to FIG. 6, the clasp 40 can be advanced along the wire 30 using a pusher catheter (not shown) or other means known in the art, as described in more detail below. The clasp 40 can have a locked configuration and an unlocked configuration. The clasp 40 can be advanced toward the bend 33 in the unlocked configuration. The clasp 40 can be prevented from moving away from the bend 33 when the clasp 40 is in the locked configuration. In some embodiments, the clasp 40 can have an actuation means (not shown) that can move the clasp 40 from the unlocked to the locked configuration. For example, the clasp 40 can have a spring-loaded locking means that is held open by a lever (not shown). Pulling on a suture (not shown) can move the lever such that the spring-loaded locking means is freed to move into the locked configuration, thereby preventing the clasp 40 from moving away from the bend 33. In some embodiments, the clasp 40 can be reversibly moved between the locked and unlocked configuration. The anchoring assembly 200 can be placed in the secured configuration by locking the clasp 40 after the clasp 40 compresses the pacemaker or ICD lead 22 between the clasp 40 and the bend 33 of the wire 30, thereby preventing the anchoring assembly 200 from sliding along the lead 22. The anchoring assembly 200 can be in the tracking configuration with the locking clasp 40 in the locked position provided the clasp 40 is sufficiently spaced apart from the bend 33 to prevent the clasp 40 from compressing the lead 22 between the clasp 40 and the bend 33, thereby allowing the anchoring assembly 200 to slide along the lead 22.

In use, a pusher catheter can advance the clasp 40 along the wire 30 toward the bend 33 in the unlocked configuration. As shown in FIG. 6, the clasp 40 can be positioned relative to the bend 33 such that an anchoring assembly 200 having a loose, hoop-like structure is formed around the lead 22. The clasp 40 can be help in place relative to the wire 30 by a pusher catheter or by temporarily moving the clasp 40 into its locked configuration. The loose, hoop-like structure of the anchoring assembly 200 can correspond to a tracking configuration of the anchoring assembly 200 in that the anchoring assembly 200 is free to slide along the pacemaker or ICD lead 22 in a monorail fashion.

A catheter (not shown) can be used to push the anchoring assembly 200 (e.g., the clasp 40) along the lead 22 and into the right ventricle 16. The anchoring assembly 200 can be pushed along the lead 22 by a steerable catheter or other means known in the art. Once the anchoring assembly 200 is positioned as desired along the pacemaker or ICD lead 22, the anchoring assembly 200 can be moved into the secured configuration to fix the position of the anchoring assembly 200 along the lead 22. In the illustrated embodiment, the anchoring assembly 200 can be moved into the secured configuration by pushing the clasp 40 further along the wire 30 toward the bend 33 until the clasp 40 pinches the lead 22 between the bend 33 and the clasp 40. The clasp 40 can pinch the lead 22 by having a surface of the clasp 40 contact the lead 22 and press the lead 22 into the bend 33 thereby increasing a frictional force between the lead 22 and the anchoring assembly 200 (e.g., the clasp 40 and the bend 33). The clasp 40 can be forced against the bend 33 to pinch the lead 22 between the clasp 40 and the bend 33, thereby fixing the wire 30 and the clasp 40 to the lead 22. The clasp 40 can then be moved into the locked configuration to prevent the clasp 40 from backing off of the wire, thereby preventing the wire 30 and the clasp 40 from moving along a longitudinal axis of the lead 22.

Figure 7:
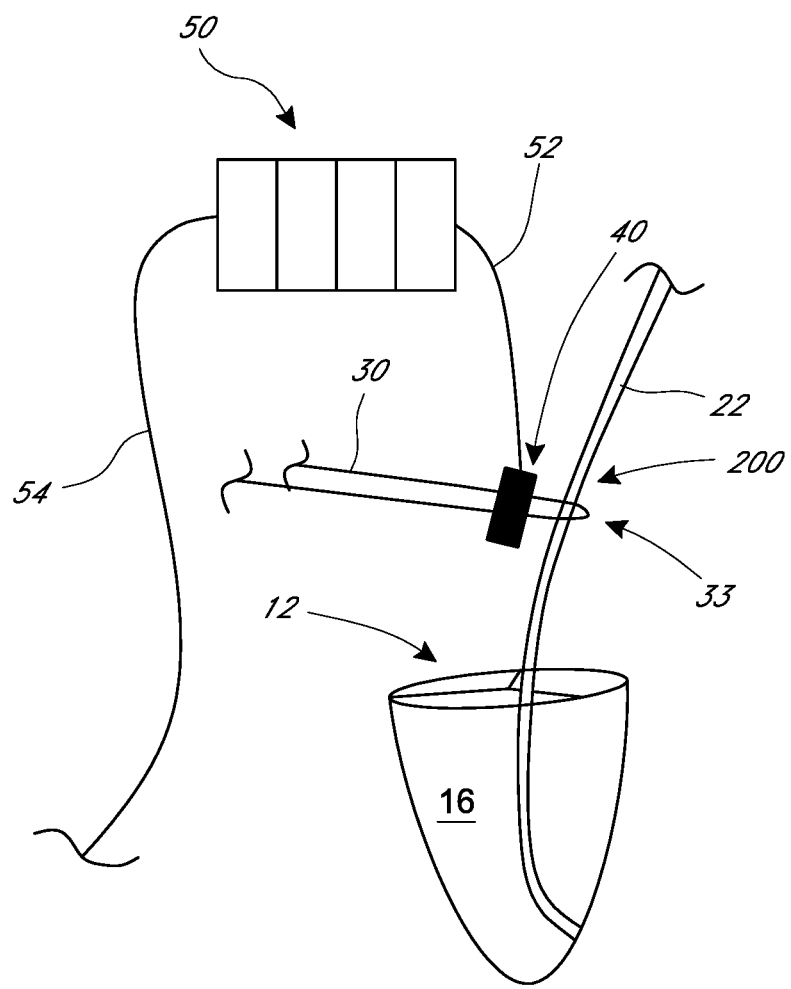
FIG. 7 depicts an embodiment of a TR-treatment device attached to the anchoring clasp of FIG. 5.

FIG. 7 illustrates a TR-treatment device 50 (e.g., balloon occluder, shunt, umbrella, one-way valve) can be attached to the clasp 40. In some embodiments, the TR-treatment device 50 can be attached to the clasp 40 after the clasp 40 has been locked onto the pacemaker or ICD lead 22. The clasp 40 can be advanced down the wire 30 and fixed to the lead 22, as described above. The TR-treatment device 50 can then be advanced down the wire 30 and secured to the clasp 40 that is already fixed onto the lead 22. In some variants, the clasp 40 has the TR-treatment device 50 pre-attached to the clasp 40 before the clasp 40 is advanced down the wire 30. In this "pre-attached" embodiment, the TR-treatment device 50 is advanced with the clasp 40 along the wire 30 when the clasp 40 is fixed to the pacemaker or ICD lead 22. As shown in FIG. 7, the TR-treatment device 50 can be attached to the clasp 40 by a distal tether 52. The TR-treatment device 50 can include a proximal tether 54. The distal and proximal tethers 52, 54 are described in more detail below.

For the sake of clarity, FIGS. 3-7 illustrate that the positioning of the wire 30 around the pacemaker or ICD lead 22 and the advancement of the clasp 40 along the wire 30 can be performed upstream of the tricuspid valve 12. However, in some embodiments one or more of the procedures for positioning of the wire 30 around the lead 22 and advancing the clasp 40 along the wire 30 can be performed downstream of the tricuspid valve 12 (e.g., within the right ventricle 16).

Figure 8:
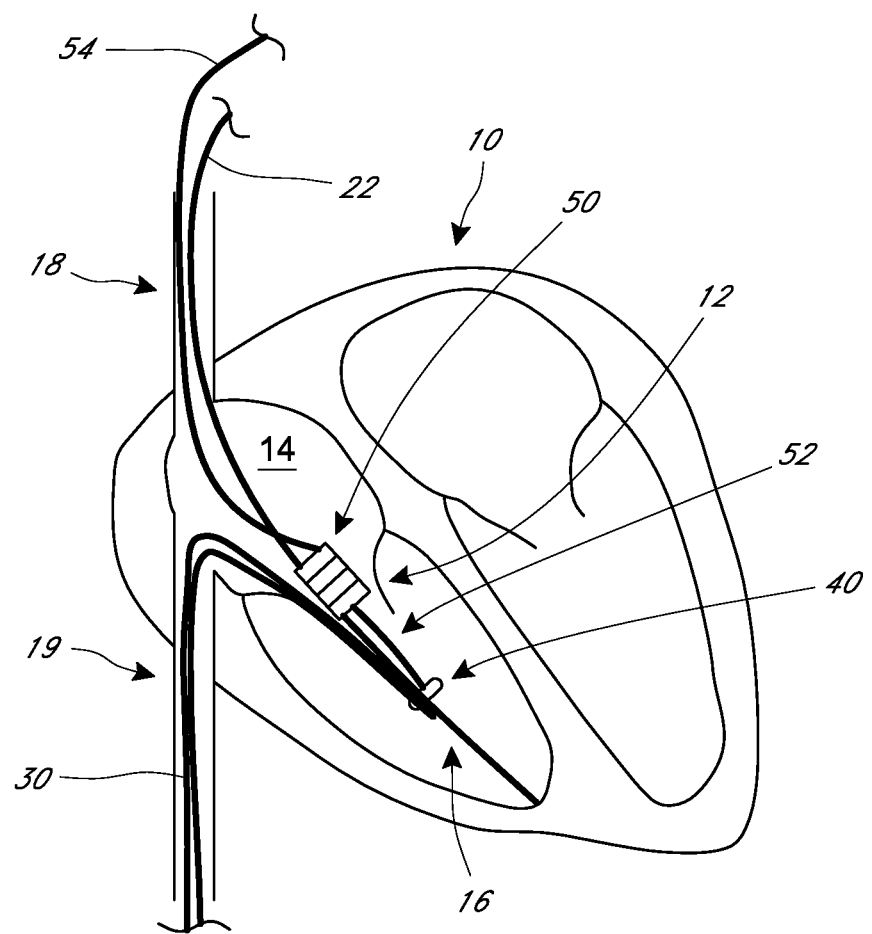
FIG. 8 depicts the embodiment of the TR-treatment device of FIG. 7 secured to a medical device lead.

FIG. 8 shows the placement of a TR-treatment device 50 within the heart 10. The FR-device 50 is attached to a clasp 40 that has been secured to an existing pacemaker or ICD lead 22. The lead 22 passes through the tricuspid valve 12 and is anchored in a wall of the right ventricle 16. The clasp 40 is secured to a portion of the lead 22 that is disposed within the right ventricle 16. As described above, the TR-treatment device 50 is attached to the clasp 40 by a distal tether 52. The distal tether 52 is sized so that the TR-treatment device 50 is positioned within the tricuspid valve 12 when the clasp 40 is fixed onto the pacemaker or ICD lead 22. In the illustrated embodiment, the TR-treatment device 50 also includes a proximal tether 54. As described in more detail below, the proximal tether 54 can provide an additional anchorage point for the TR-treatment device 50. In some arrangements, the proximal tether 54 is configured to allow adjustment of the TR-treatment device 50, as discussed below.

With continued reference to FIG. 8, the proximal tether 54 can extend through the superior vena cava 18. The wire 30 along which the clasp 40 is advanced to anchor the clasp 40 to the lead 22 is shown extending away from the heart 10 through the inferior vena cava 19. In some arrangements, the proximal tether 54 can extend away from the heart 10 through the inferior vena cava 19. In certain variants, the wire 30 can extend away from the heart through the superior vena cava 18. The wire 30 and the proximal tether 54 are shown in different vessels for the sake of clarity. In some arrangements, at least a portion of the wire 30 and the proximal tether 54 can run together through the same vessel.

Figure 9:
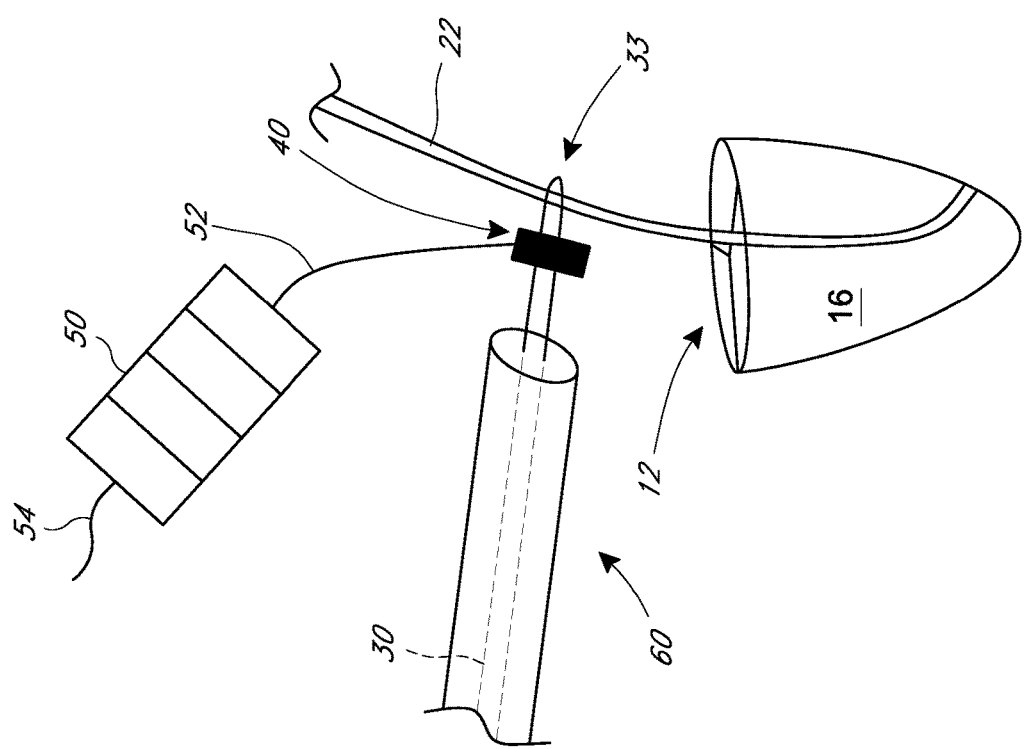
FIG. 9 depicts a pusher catheter advancing the anchoring clasp of FIG. 5 along the wire toward the medical device lead.

FIG. 9 shows a pusher catheter 60 that can be used to advance the clasp 40 along the wire 30 toward the bend 33 to secure the clasp 40 onto the pacemaker or ICD lead 22. In the illustrated embodiment, the clasp 40 is pre-attached to a TR-treatment device 50 by a distal tether 52. The TR-treatment device 50 includes a proximal tether 54. The pusher catheter 60 can have a distal face that abuts a proximal face of the clasp 40, allowing the pusher catheter 60 to transmit a compression force to the clasp 40 and push the clasp 40 down the wire 30 toward the bend 33. In some arrangements, the distal face of the pusher catheter 60 can have an attachment feature that is configured to engage with a mating feature on the proximal face of the clasp 40 and is adapted to move the clasp 40 into the locked configuration. For example, the distal face of the pusher catheter 60 can have a fin (not shown) that fits into a groove (not shown) on the proximal face of the clasp 40. Rotation of the pusher catheter 60 about its longitudinal axis can deform the clasp 40 into a locked configuration.

Figure 10:
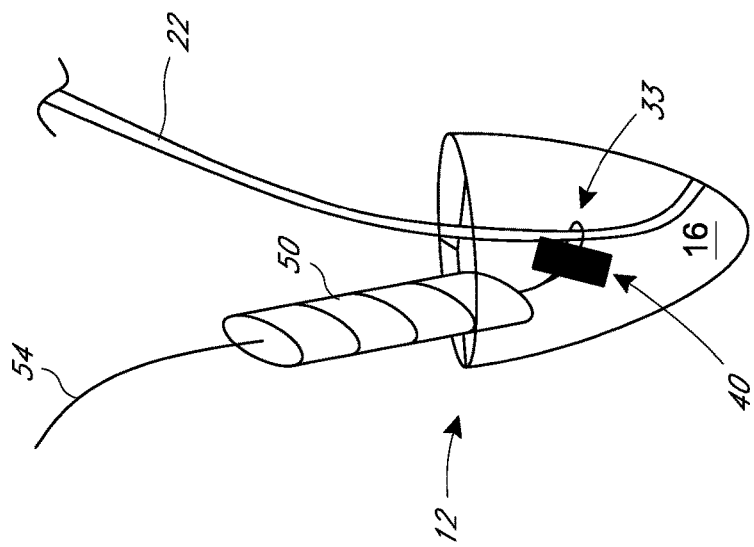
FIG. 10 depicts an embodiment of a TR-treatment device secured to a medical device lead that is anchored in a ventricular wall of a heart.

The pusher catheter 60 can include a means for cutting the wire 30 after the clasp 40 has been locked onto the lead 22. The pusher catheter 60 can include means for capping the cut wire 30 so that the sharp edges of the cut wire 30 are not exposed to the surrounding tissue. FIG. 10 illustrates a TR-treatment device 50 secured to a lead 22 through an intermediary clasp 40. The wire 30 that was used to deliver the clasp 40 to the lead 22 has been trimmed and removed by the pusher catheter 60, as described above.

Figure 11B:
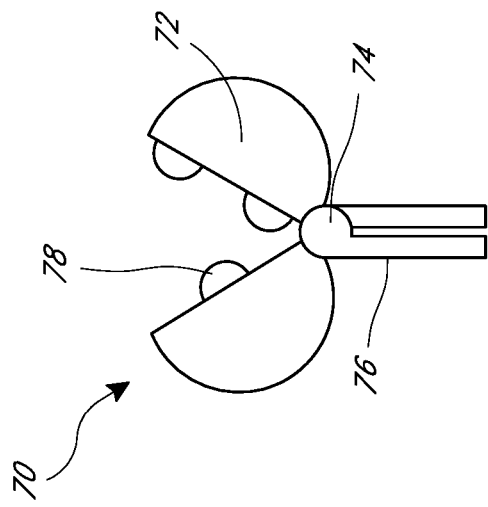
FIG. 11B depicts the clamp of FIG. 11A in the open position.
Figure 11A:
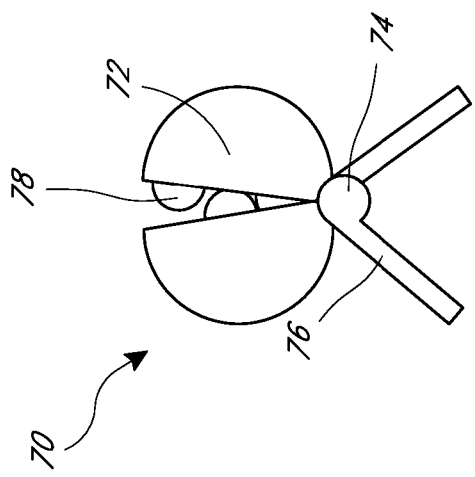
FIG. 11A depicts an embodiment of a clamp in a clamped an at-rest position.

FIGS. 11A-B illustrate a clamp 70 that can provide another arrangement for forming an anchoring assembly 200 that positions and secures a TR-treatment device 50 on an existing pacemaker or ICD lead 22. The clamp 70 can have a pair of opposing jaws 72 that are joined together by a hinge 74. The hinge 74 can include a spring (not shown) that is adapted to force the jaws 72 together when the clamp 70 is in its rest position, as shown in FIG. 11A. The clamp 70 can include a pair of legs 76. The legs 76 can be pivotly coupled to the jaws 72 by the hinge 74 such that when the legs 76 are pinched together the jaws 72 are forced open, as shown in FIG. 11B. The jaws 72 can include one or more grip features 78 that are disposed on the clamping faces of the jaws 72, as shown in FIGS. 11A and 11B. The grip features 78 can enhance the ability of the jaws 72 to clamp onto an element disposed between the jaws 72 when the jaws 72 are in the rest position (FIG. 11A).

Figure 12:
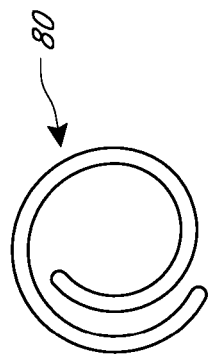
FIG. 12 depicts a wrapped coil that can be used to hold the clamp in the open position.

FIG. 12 illustrates an elastic coil 80 that is configured to partially unravel when the coil 80 is unconfined. The coil 80 can be made of a thin metal or other elastic material known in the art. As described in more detail below, the coil 80 can be used to hold the legs 76 of the clamp 70 together so that the jaws 72 of the clamp 70 are open. When the coil 80 is allowed to expand, the coil 80 can unravel, allowing the legs 76 of the clamp 80 to move. When the legs 76 of the clamp are unrestrained, the spring in the hinge 74 can force the legs 76 apart, thereby driving together the jaws 72 and allowing the clamp 70 to clamp onto an element disposed between the jaws 72.

Figure 13B:
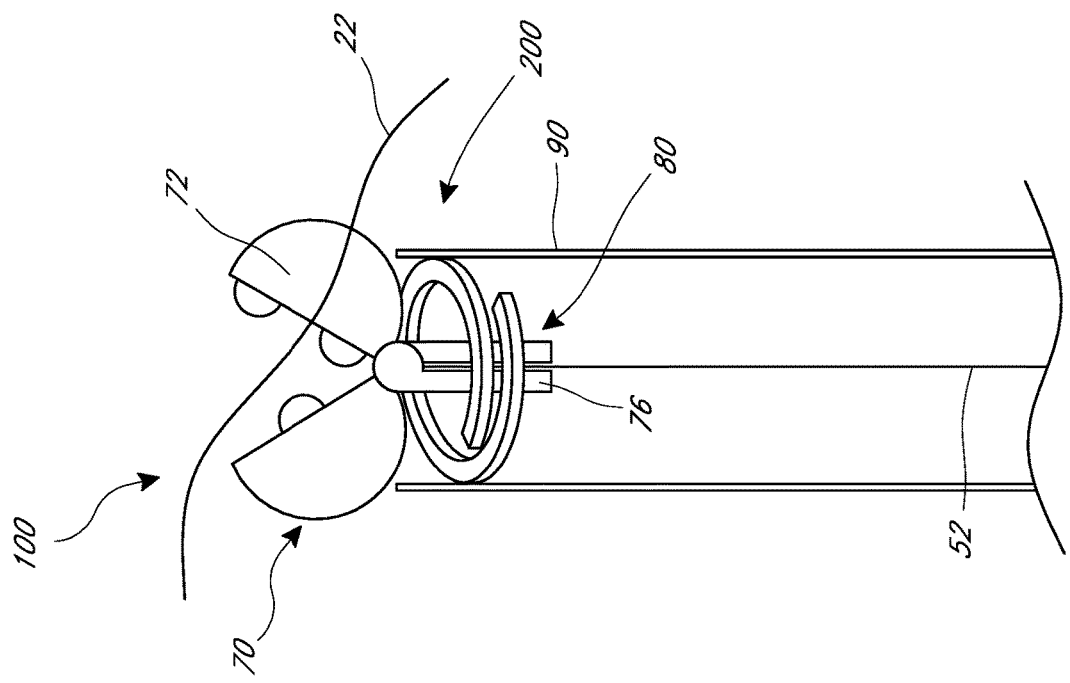
FIG. 13B depicts the delivery device of FIG. 13A partially deployed from the delivery sheath.
Figure 13A:
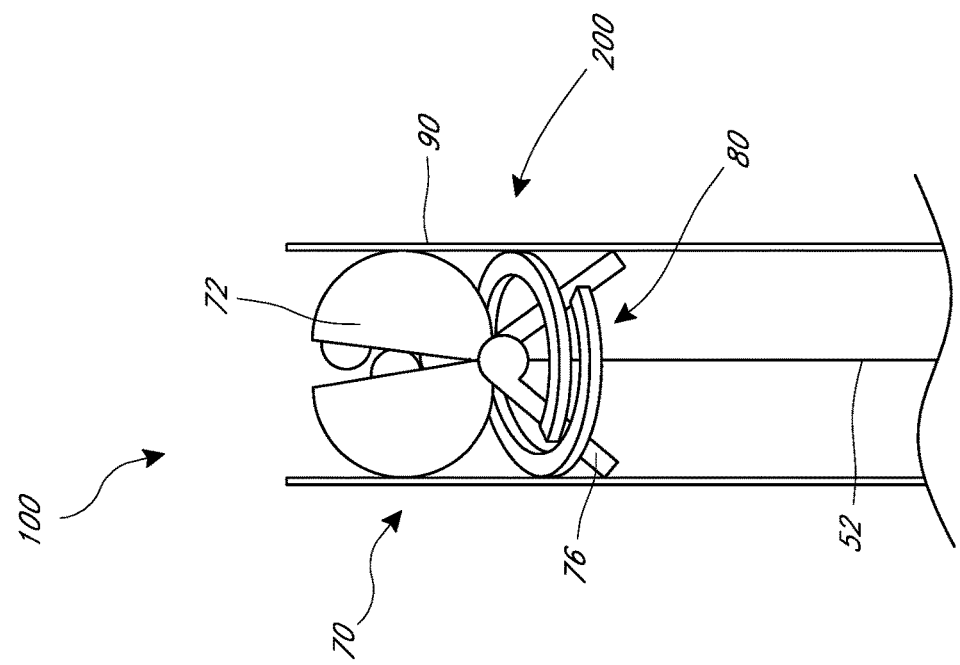
FIG. 13A depicts an embodiment of a delivery device having a clamp with the clamp fully seated within a delivery sheath.
Figure 13C:
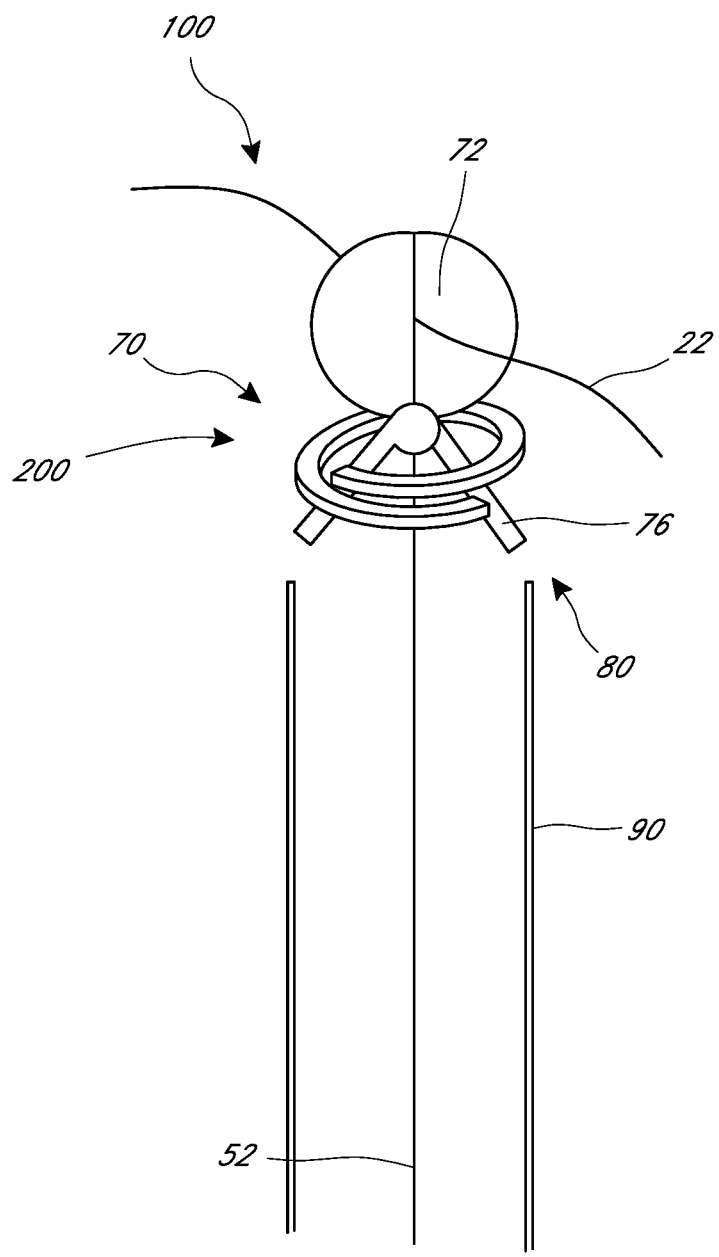
FIG. 13C depicts the delivery device of FIG. 13A fully deployed from the delivery sheath.

FIGS. 13A-C illustrate an embodiment of a delivery device 100 having a clamp 70 and a coil 80 that are arranged to form an embodiment of an anchoring assembly 200, as described in more detail below. The clamp 70 can be attached to a TR-treatment device 50 (not shown) by a distal tether 52, as described above. FIG. 13A shows the clamp 70 fully contained within a delivery sheath 90 of the delivery device 100. The coil 80 is wound around the legs 76 of the clamp 70, providing a force that tends to drive the legs 76 toward one another. The sheath 90 prevents the coil 80 from unwinding to its relaxed configuration. The force from the wrapped coil 80 would cause the jaws 72 to pivot away from one another about the hinge 74 if the jaws 72 were unconstrained. However, the jaws 72 are constrained by the sheath 90. Therefore, when the jaws 72 are within the sheath 90, the force of the coil 80 is unable to drive the legs 76 toward one another.

FIG. 13B shows the clamp 70 partially deployed from the sheath 90 of the delivery device 100. The jaws 72 exit the distal end of the sheath 90 while the legs 76 and the coil 80 remain within the sheath 90. The sheath 90 continues to constrain the coil 80 in its wrapped up configuration. The wrapped coil 80 forces the legs 76 toward one another. Because the jaws 72 are free of the sheath 90, the coil 80 is able to move the legs 76 toward one another, causing the jaws 72 to pivot apart from one another. The delivery device 100 is positioned so that the pacemaker lead or ICD lead 22 extends through the open jaws 72 of the clamp 70.

FIG. 13C shows the clamp 70 deployed farther from the sheath 90 such that the coil 80 is outside of the sheath 90. The coil 80 is unconstrained by the sheath 90 and can unwind to its relaxed configuration. The unwinding of the coil 80 releases the legs 76, allowing the spring-loaded hinge 74 of the clamp 70 to pivot the jaws 72 toward one another. The jaws 72 clamp down on the pacemaker or ICD lead 22 that was positioned between the jaws 72, thereby securing the clamp 70 to the existing lead 22. The coil 80 can be retained by a tether (not shown) to allow the coil 80 to be withdrawn from the patient. The sheath 90 can be further retracted to release the TR-treatment device (not shown) that is attached to the clamp 70 by the distal tether 52.

In some embodiments, the clamp 70, the coil 80, and the sheath 90 can be arranged to form an anchoring assembly 200 that has a tracking configuration and a secured configuration as described previously. For example, the jaws 72 of the clamp 70 can be arranged to form a loop around the pacemaker or ICD lead, corresponding to a tracking configuration that allows the anchoring assembly 200 to slide along the lead 22. The clamp 70 can be further configured so that the jaws 72 can pivot further toward or past one another, thereby clamping the lead 22 between the jaws 72 and corresponding to a secured configuration of the anchoring assembly 200. Although not shown, the sheath 90 can be arranged so that the inner diameter of the sheath 90 expands in a step-wise fashion in the direction of the distal end of the sheath 90. The sheath 90 can have a proximal region and a distal region. The inner diameter of the sheath 90 in the proximal region can be less than the inner diameter of the sheath 90 in the distal region. In this way, the coil 80 can relax to a greater extent in the distal region than in the proximal region, while still being confined by the sheath 90. When the coil 80 is the proximal region and the jaws 72 are outside of the sheath 90, the jaws 72 are open to receive the pacemaker or ICD lead 22 (FIG. 13B). When the clamp 70 is advanced distally to bring the coil 80 into the distal region of the sheath 90, the jaws 72 pivot toward one another to form an anchoring assembly 200 in a tracking configuration. The coil 80 can be advanced outside of the sheath 90, allowing the coil 80 to relax completely such that the jaws 72 pivot further toward or past one another (not shown) to secure the clamp 70 onto the lead 22, thereby placing the anchoring assembly 200 in the secured configuration.

Figure 14B:
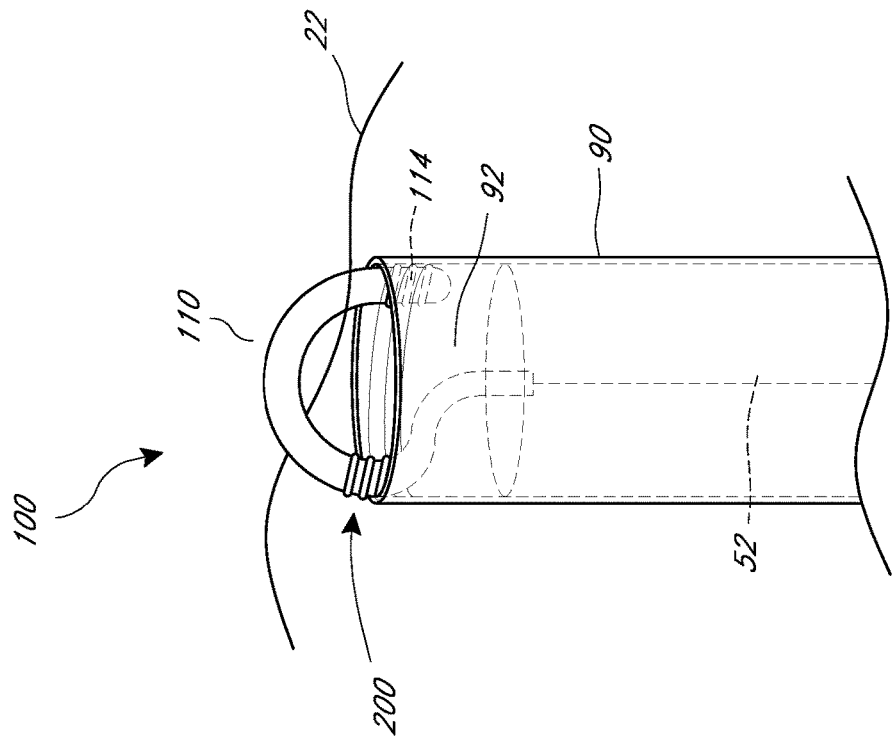
FIG. 14B depicts the delivery device of FIG. 14A with the scored hook attached to the distal end of the delivery sheath.
Figure 14A:
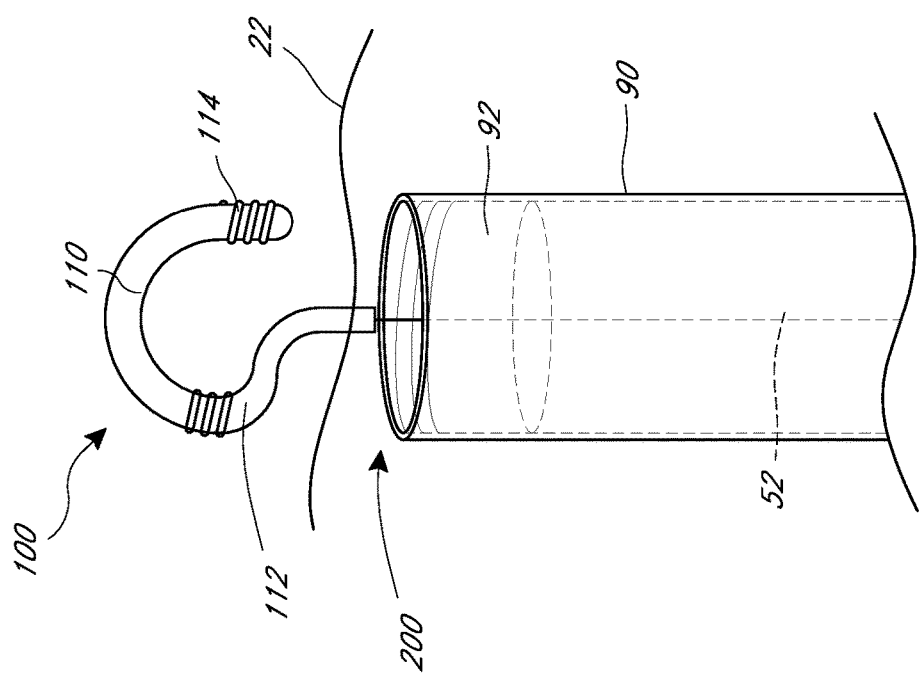
FIG. 14A depicts an embodiment of a delivery device having a scored hook for securing the medical device lead.

FIGS. 14A-B illustrate an embodiment of an anchoring assembly 200 of a delivery device 100 having a threaded hook 110 for anchoring a TR-treatment device (not shown) to a pacemaker or ICD lead 22. The threaded hook 110 can have grooves or an external thread on a shank 112 and tip 114 of the hook 110, as indicated in FIG. 14A. The hook 110 can be attached to a TR-treatment device (not shown) by a distal tether 52. The delivery sheath 90 can have a detachable distal end 92. The hook 110 can be extended distal of the detachable distal end 92 of the delivery sheath 90 and hooked over the lead 22, as shown in FIG. 14A.

FIG. 14B shows that after the hook 110 captures the lead 22, the hook 110 can be drawn back to engage the distal end 92 of the delivery sheath 90. The distal end 92 can have an external or internal thread that mates with the grooves or external thread on the shank 112 and tip 114 of the hook 110. The hook 110 and the distal end 92 can be rotated relative to one another to screw the hook 110 onto the distal end 92, trapping the lead 22 between the hook 110 and the distal end 92 of the sheath 90. The inner curved surface of the hook 110 can be spaced apart from the distal end 92 thereby forming an anchoring assembly 200 in the tracking configuration. The anchoring assembly 200 can be slid along the pacemaker or ICD lead 22 as described previously to position the anchoring assembly 200 at a desired location along the lead 22. Once the anchoring assembly 200 is in the desired location, the distal end 92 can be further rotated relative to the hook 110 to draw the hook 110 toward the distal end 92 and pinching the lead 22 between the hook 110 and the distal end 92, forming an anchoring assembly 200 in the secured configuration. Further twisting of the hook 110 and the distal end 92 relative to one another can cause the distal end 92 to detach from the delivery sheath 90, leaving the hook 110 anchored onto the lead 22.

Figure 15:
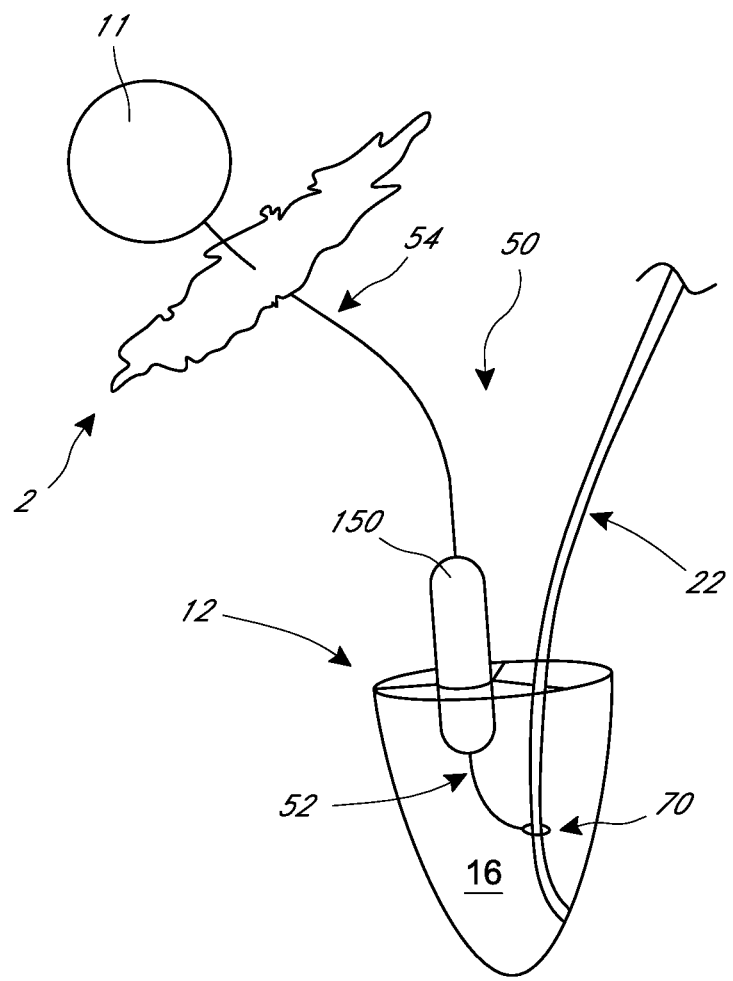
FIG. 15 depicts an embodiment of a TR-treatment device having an adjustable balloon occluder.

FIG. 15 illustrates an embodiment of the TR-treatment device 50 that has a balloon occluder 150. A proximal tether 54 extends from the balloon occluder 150 to the skin 2 of the patient. The proximal tether 54 includes a hollow lumen that fluidically connects the interior of the balloon occluder 150 with a port 11 disposed at or near the skin 2 of the patient. The port 11 can be adapted to allow the size of the balloon occluder to be adjusted by injecting or withdrawing filler material (e.g., saline) through the port 11. In the illustrated embodiment, the balloon occluder 150 is attached to a clamp 70 by a distal tether 52. The balloon occluder 150 can be attached to the lead 22 by other anchoring means disclosed herein (e.g., a clasp 40, a scored hook 110). The clamp 70 is secured to the lead 22. The distal tether 52 is sized so that the balloon occluder 150 extends across the tricuspid valve 12 when the clamp 70 is fixed to the lead 22. In some embodiments, the port 11 enables the size of the balloon occluder 150 to be adjusted over time to accommodate remodeling of the annulus of the valve 12. In certain arrangements, the port 11 allows the size of the balloon occluder 150 to be customized to the valve anatomy of the patient during implantation of the TR-treatment device 50.

Figure 16:
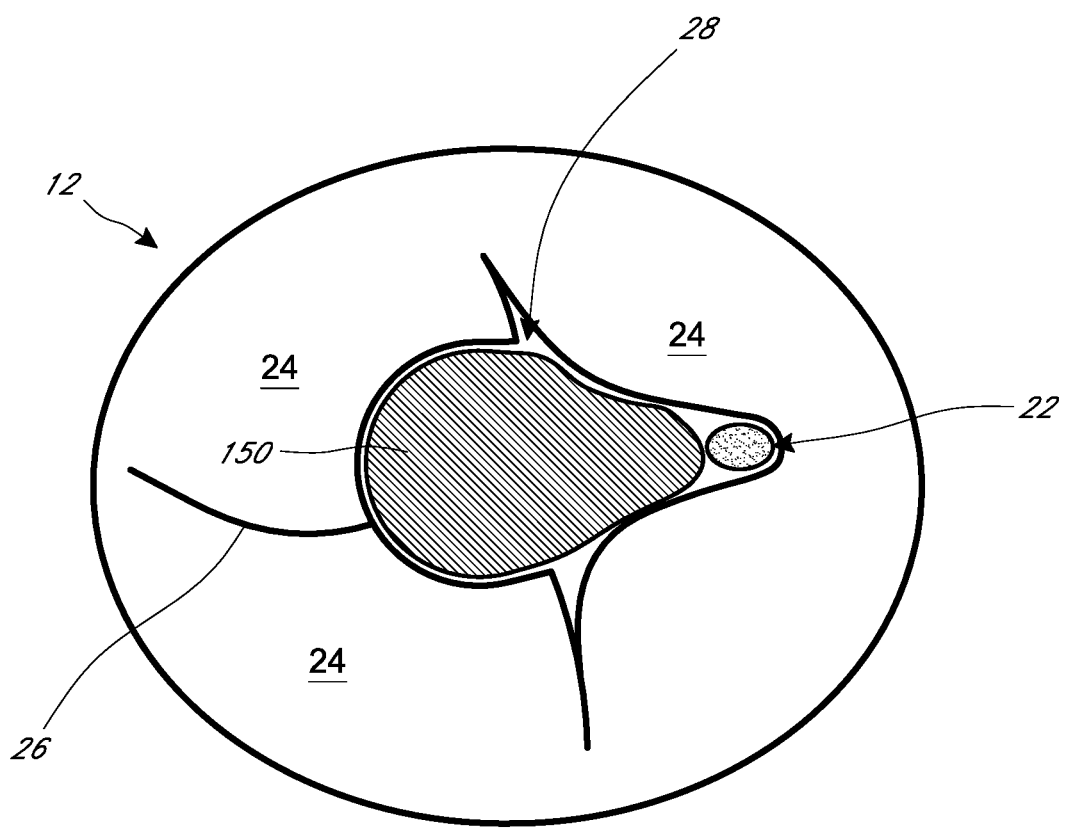
FIG. 16 depicts a top view of a tricuspid valve with a balloon occluder and a medical device lead extending across the valve.

FIG. 16 is a top view of a tricuspid valve 12 with a pacemaker or ICD lead 22 and balloon occluder 150 positioned within the valve 12. As discussed above, the lead 22 can interfere with the leaflets 24 forming a complete line of coaptation 26 with one another. The interference of the lead 22 with the leaflet 24 can cause a gap 28 to remain between the leaflets 24 during systole. As shown in FIG. 16, the balloon occluder 150 can be adapted to occupy a large portion of the gap 28. In the illustrated embodiment, the lead 22 causes an asymmetric gap 28 to be formed between the leaflets 24. The balloon occluder 150 can be shaped to match the gap 28 that is caused by the lead 22. In the illustrated embodiment, the balloon occluder 150 has a pear-shaped transverse cross-section, with the stem portion of the pear shape disposed between the lead 22 and the base portion of the pear shape, as shown in FIG. 16.

Figure 17B:
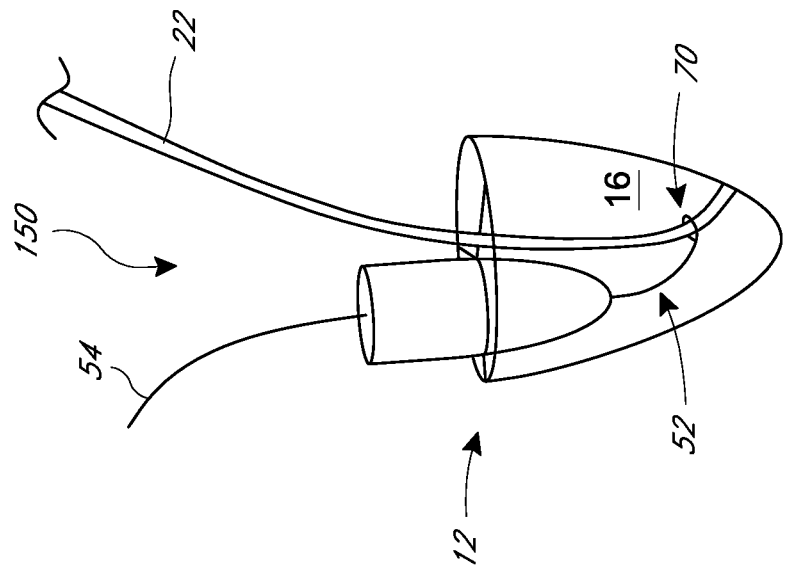
FIG. 17B depicts a side view of a tricuspid valve with a conical balloon occluder anchored to a medical device lead and seated in a tricuspid valve of a heart.
Figure 17A:
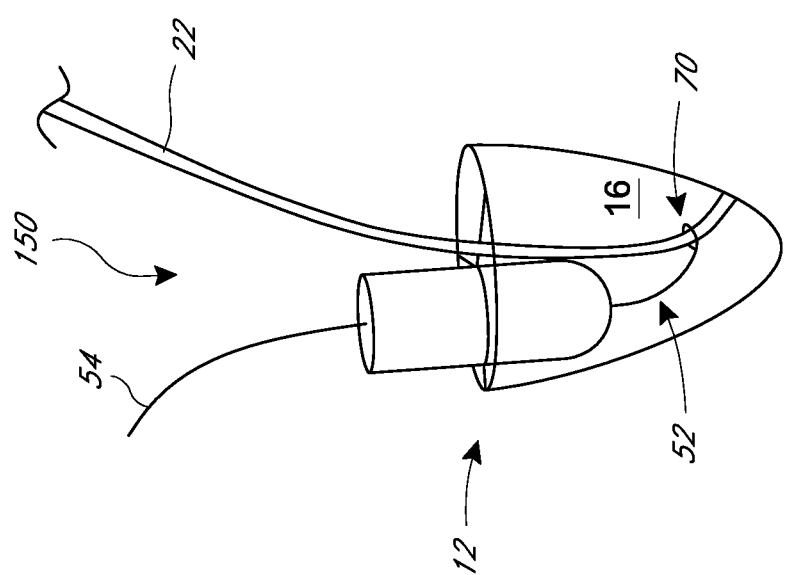
FIG. 17A depicts a side view of a tricuspid valve with a cylindrical balloon occluder anchored to a medical device lead and seated in a tricuspid valve of a heart.
Figure 17D:
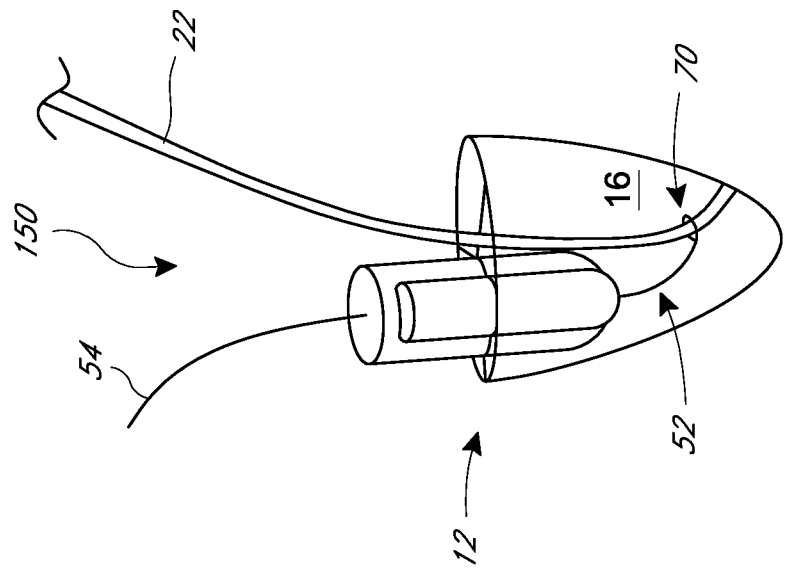
FIG. 17D depicts a side view of a tricuspid valve with a dual-balloon occluder anchored to a medical device lead and seated in a tricuspid valve of a heart.
Figure 17C:
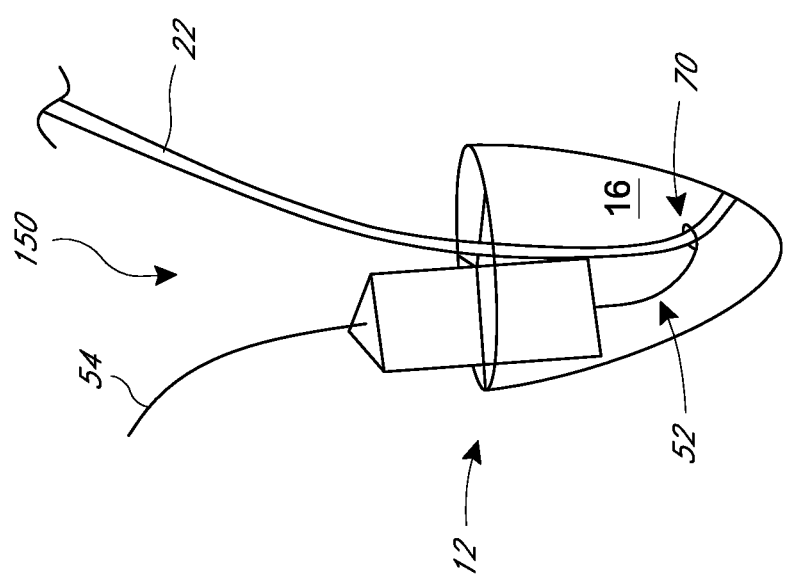
FIG. 17C depicts an asymmetric balloon occluder anchored to a medical device lead and seated in a tricuspid valve of a heart.
Figure 17E:
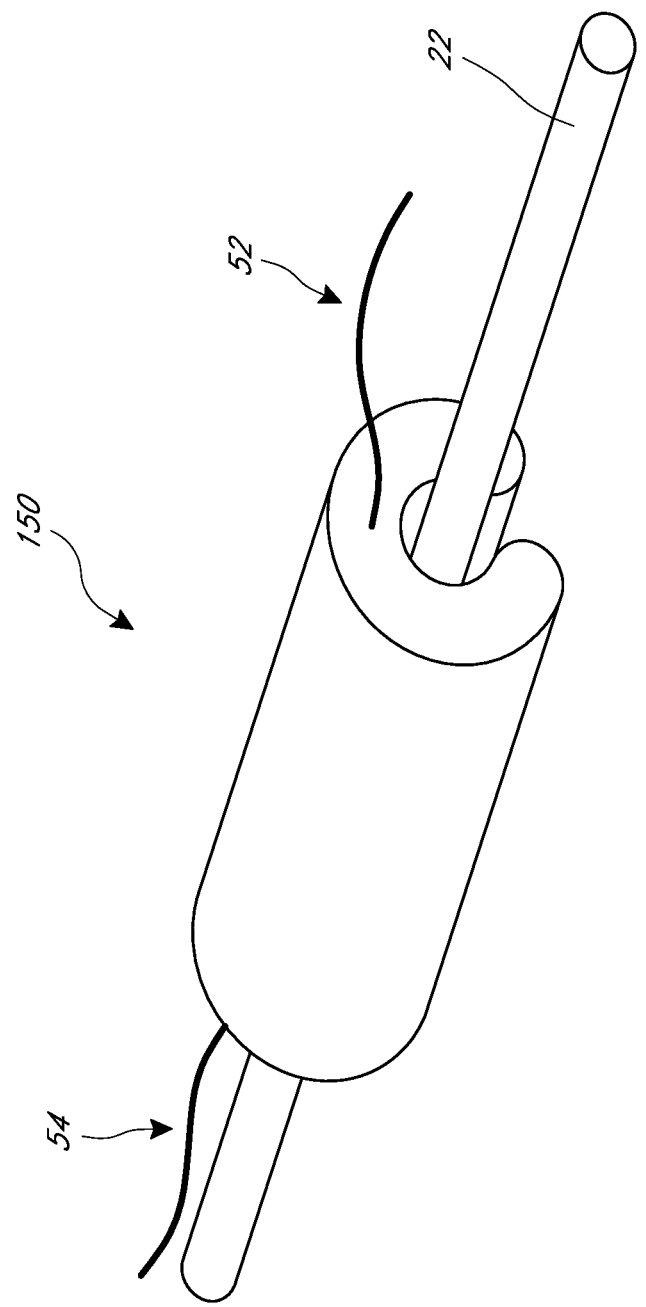
FIG. 17E depicts a perspective view of a tricuspid valve with a grooved balloon occluder anchored to a medical device lead and seated in a tricuspid valve of a heart.

FIGS. 17A-E show other shapes the balloon occluder 150 can have. FIG. 17A depicts a cylindrical balloon occluder 150 that has a substantially uniform transverse cross-section along the longitudinal axis of the balloon occluder 150. FIG. 17B shows the balloon occluder 150 can have a cone shape that tapers in the direction from the right atrium 14 to the right ventricle 16. FIG. 17C illustrates the balloon occluder 150 can have an asymmetrical shape. FIG. 17D shows the balloon occluder 150 can include two or more balloons coupled together. FIG. 17E depicts a balloon occluder 150 that has a groove extending longitudinally along a face of the occluder, with the groove being shaped to receive the lead 22.

Figure 18:
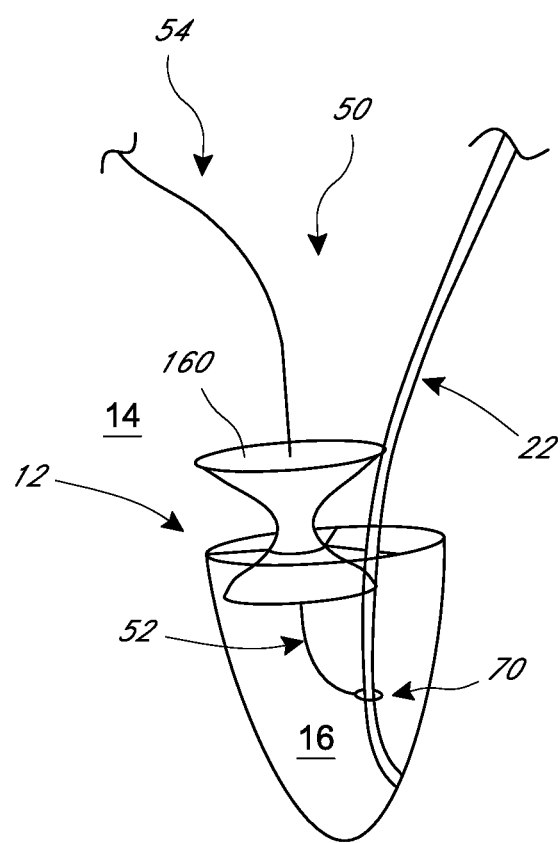
FIG. 18 depicts a side view of a tricuspid valve with a one-way valve occluder anchored to a medical device lead and seated in a tricuspid valve of a heart.

FIGS. 18-21 show that the TR-treatment device 50 can have a TR-reducing member that takes a form other than the balloon occluder 150 described previously. FIG. 18 shows that the TR-treatment device 50 can include a one-way valve 160. In the illustrated embodiment, the one-way valve 160 is attached to the clamp 70 by a distal tether 52. The clamp 70 is secured to the pacemaker or ICD lead 22. The one-way valve 160 can be secured to the lead 22 by other anchoring means disclosed herein (e.g., a clasp 40, a scored hook 110). The one-way valve 160 can be configured to allow blood flow from the right atrium 14 to the right ventricle 16 (antegrade flow) while preventing or inhibiting blood flow from the right ventricle 16 to the right atrium 14 (retrograde flow).

Figure 19B:
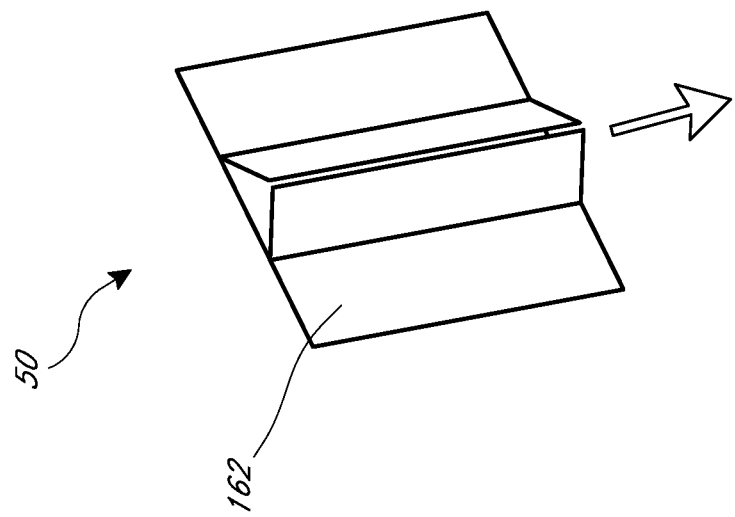
FIG. 19B depicts the movable flap occluder of FIG. 19A in an open position to allow antegrade flow.
Figure 19A:
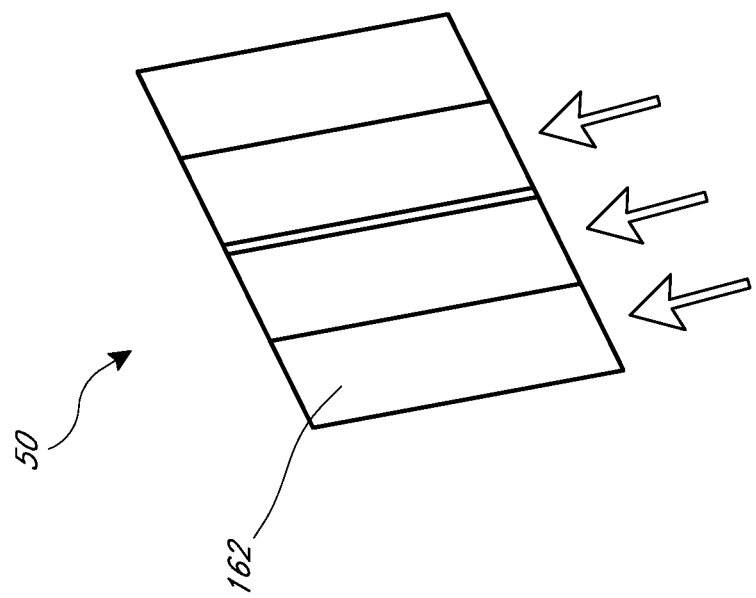
FIG. 19A depicts a movable flap occluder in a closed position to prevent retrograde flow.

FIG. 19A-B show a TR-treatment device 50 that have movable flaps 162 to achieve a one-way valve function. The flaps 162 can be arranged as a plurality of parallel flaps 162 that seal when exposed to retrograde flow (FIG. 19A). The flaps 162 can pivot to create gaps therebetween when exposed to antegrade flow (FIG. 19B).

Figure 20:
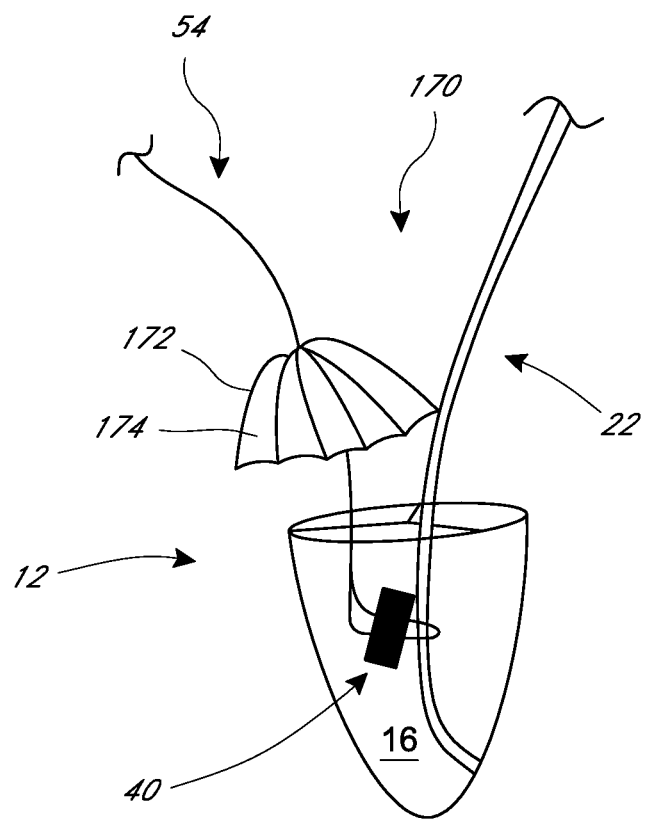
FIG. 20 depicts an umbrella-shaped occluder anchored to a medical device lead and seated in a tricuspid valve of a heart.

FIG. 20 shows an umbrella- or parachute-shaped occluder 170. The umbrella-shaped occluder 170 is anchored to a pacemaker or ICD lead 22 with a clasp 40, as discussed above. The umbrella-shaped occluder 170 can be attached to the lead 22 by other anchoring means disclosed herein (e.g., a clamp 70, a scored hook 110). As shown in FIG. 20, the umbrella-shaped occluder 170 can be oriented so that the peak of the umbrella faces into the right atrium and away from the tricuspid valve 12. The umbrella-shaped occluder 170 can have a plurality of collapsible struts 172 that radiate away from the peak of the umbrella. A membrane 174 can extend between the struts 172. The struts 172 can collapse radially inward under antegrade flow, thereby allowing diastolic blood flow to pass through the tricuspid valve 12. The struts 172 can flare radially outward under retrograde flow, thereby preventing or inhibiting systolic blood flow from passing through the tricuspid valve 12.

Figure 21:
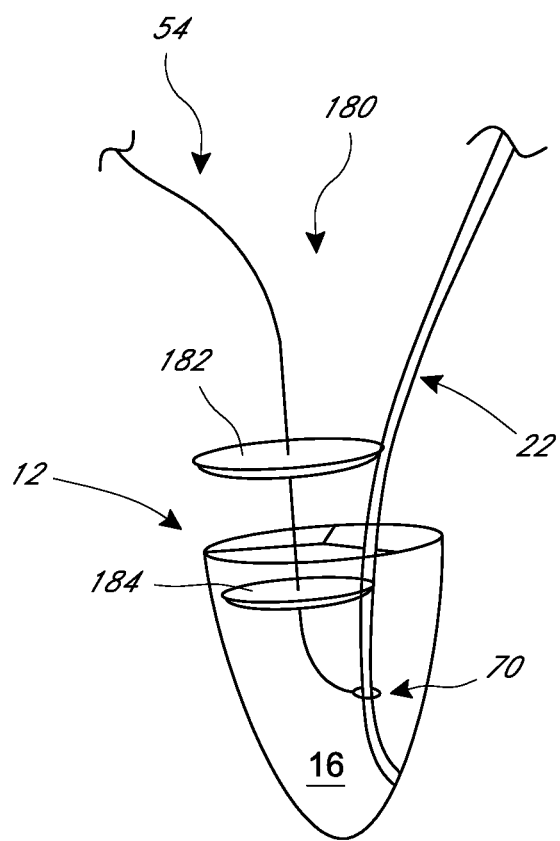
FIG. 21 depicts a seawall-shaped occluder anchored to a medical device lead and seated across a tricuspid valve of a heart.

FIG. 21 shows a seawall-shaped occluder 180. The seawall-shaped occluder 180 is anchored to a pacemaker or ICD lead 22 with a clamp 70, as discussed above. The seawall-shaped occluder 180 can be attached to the lead 22 by other anchoring means disclosed herein (e.g., a clasp 40, a scored hook 110). As shown in FIG. 21, the seawall-shaped occluder 180 can have a discoid atrial occluder 182 that is disposed on the atrial side of the tricuspid valve 12. The seawall-shaped occluder 180 can have a discoid ventricular occluder 184 that is disposed on the ventricular side of the tricuspid valve 12, as shown in FIG. 21. The atrial occluder 182 can have a larger outer dimension compared to the ventricular occluder 184. The atrial occluder 182 and the ventricular occluder 184 can be arranged to prevent or reduce retrograde systolic flow (e.g., TR) from impacting the right atrium.

Figure 22:
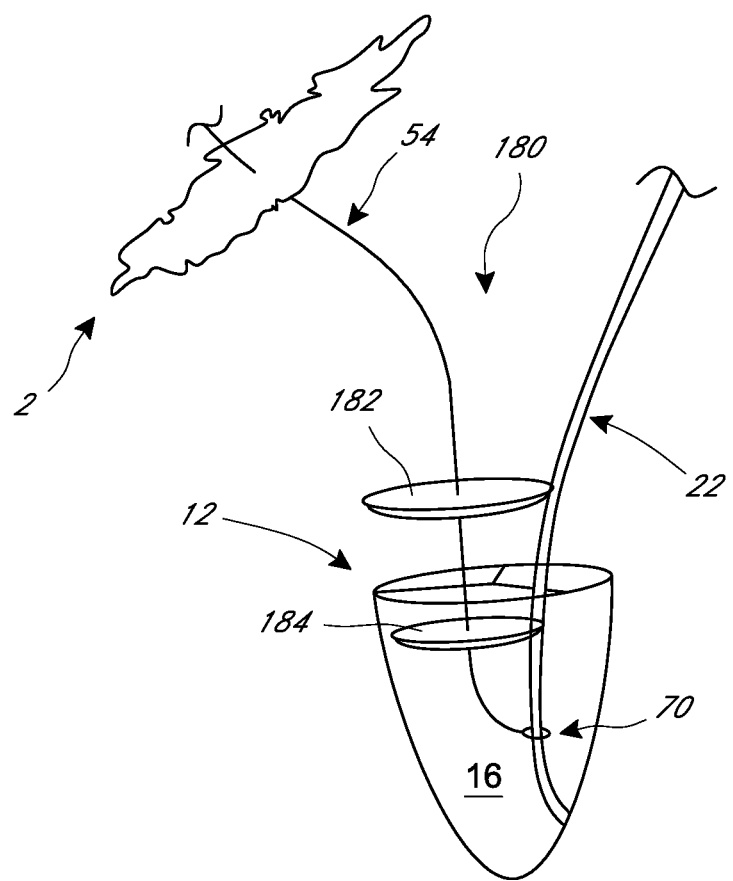
FIG. 22 depicts the seawall-shaped occluder of FIG. 21 anchored to a medical device lead through a distal tether and to the skin of a patient through a proximal tether.

FIG. 22 shows seawall-shaped occluder 180 anchored to a lead 22 with a clamp 70. The seawall-shaped occluder 180 can include a proximal tether 54 that is implanted in the skin 2 of the patient, as described above.

Figure 23:
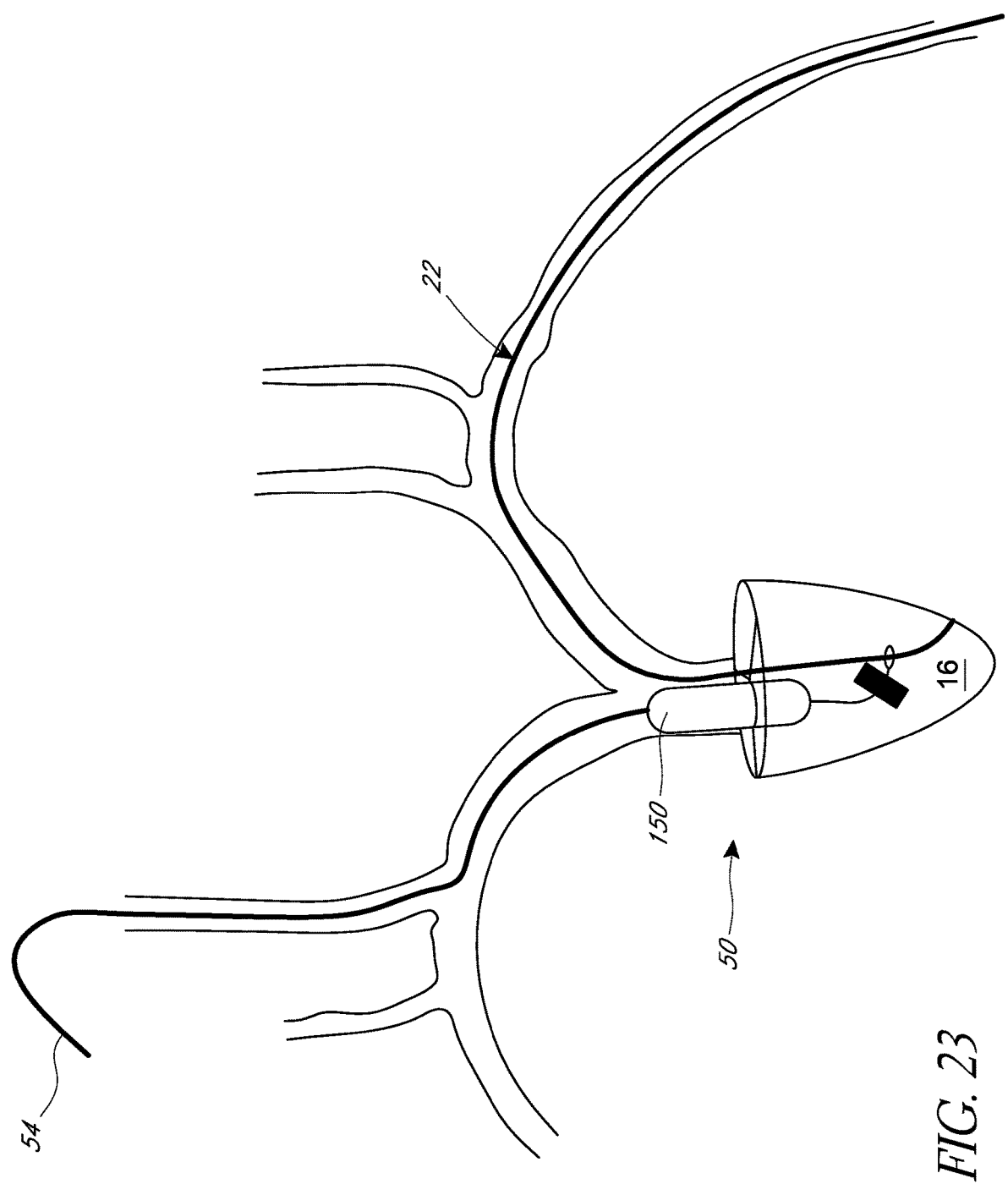
FIG. 23 depicts the different access pathways through which the TR-treatment device can be delivered to the tricuspid valve.

FIG. 23 shows the different pathways the delivery device 100 can access the lead 22. The delivery device 100 can deliver the TR-treatment device 50 through a subclavian approach (e.g., right subclavian approach), or through an inferior jugular tunneled approach (not shown). As shown in FIG. 23, the TR-treatment device 50 can include a proximal tether 54 that is implanted in a skin of the patient. The TR-treatment device 50 can be secured to the lead 22 as described above.

Although the present invention has been disclosed with reference to certain specific embodiments of devices and methods, the inventors contemplate that the invention more broadly relates to methods disclosed above, such as those useful for orienting an implant with respect to an anatomical structure, as well as performing diagnostic and/or therapeutic procedures in the heart or adjacent the heart. Accordingly, the present invention is not intended to be limited to the specific structures and steps disclosed herein, but rather by the full scope of the attached claims.

What is claimed is:

1. A cardiac valve occluder comprising:
an anchoring wire configured to provide a distal bend disposed between opposing end portions of the anchoring wire, the distal bend being configured to be disposed around a lead of a cardiac pacing device or a defibrillation device;
a locking member moveable over or along one or both of the opposing end portions of the anchoring wire and having a cinched configuration, the locking member being secured to the anchoring wire and being prevented from moving away from the distal bend when the locking member is in the cinched configuration; and
an occluder coupled to the locking member or to the anchoring wire, the occluder being arranged to inhibit a fluid flow in a direction away from the occluder and toward the locking member when the occluder is disposed in a valve annulus;
wherein the locking member is configured to retain the distal bend around the lead of the cardiac pacing device or the defibrillation device when in the cinched configuration such that the occluder is disposed within a heart valve.

2. The cardiac valve occluder of claim 1, further comprising a distal tether disposed between and defining a distance between the locking member and the occluder.

3. The cardiac valve occluder of claim 2, wherein the position of the occluder relative to the lead can be adjusted by selecting a location to apply the cinched configuration such that the occluder can be positioned in the heart valve.

4. The cardiac valve occluder of claim 1, further comprising a proximal tether that extends from the occluder in a direction that is away from the locking member.

5. The cardiac valve occluder of claim 4, wherein the proximal tether is a hollow conduit, a proximal end of the hollow conduit comprising a port that is fluidically connected to an internal space of the occluder.

6. The cardiac valve occluder of claim 1, wherein the occluder comprises a surface that is moveable between a first configuration and a second configuration, the surface being adapted such that when the surface is in the first configuration, the surface inhibits the fluid flow in the direction toward the occluder and away from the locking member to a greater extent than when the surface is in the second configuration.

7. The cardiac valve occluder of claim 1, wherein the occluder has a proximal portion and a distal portion, the distal portion being disposed between the locking member and the proximal portion, an outer dimension of the proximal portion being greater than an outer dimension of the distal portion.

8. The cardiac valve occluder of claim 1, wherein a transverse cross-section of the occluder is pear shaped.

9. The cardiac valve occluder of claim 1, wherein an internal space of the occluder is configured to be filled with a fluid.

10. The cardiac valve occluder of claim 1, wherein the occluder comprises a one-way valve.

11. A cardiac system comprising:
  a cardiac pacing device comprising an electrical lead configured to be disposed across a heart valve and thereafter secured to cardiac tissue;
  a cardiac valve backflow control device, comprising:
    an anchoring wire configured to provide a distal bend disposed between opposing end portions of the anchoring wire, the distal bend being configured to be disposed around the lead when the lead is secured to cardiac tissue;
    a locking member moveable over or along one or both of the opposing end portions of the anchoring wire and having a locked configuration, the locking member being secured to the anchoring wire and being prevented from moving away from the distal bend when the locking member is in the locked configuration, such that the distal bend is immobilized to the lead in the locked configuration; and
    an occluder coupled to the locking member or to the anchoring wire, the occluder being arranged to inhibit a fluid flow in a direction away from the occluder and toward the locking member when the occluder is disposed in a valve annulus;
  whereby the occluder of the cardiac backflow control device can be maintained in position within a valve annulus by cinching the distal bend about the lead and without direct connection to the cardiac tissue.

12. A cardiac system, comprising:
  a defibrillation device comprising an electrical lead configured to be disposed across a heart valve and thereafter secured to cardiac tissue;
  a cardiac valve backflow control device, comprising:
    an anchoring wire configured to provide a distal bend disposed between opposing end portions of the anchoring wire, the distal bend being configured to be disposed around the lead when the lead is secured to cardiac tissue;
    a locking member moveable over or along one or both of the opposing end portions of the anchoring wire and having a locked configuration, the locking member being secured to the anchoring wire and being prevented from moving away from the distal bend when the locking member is in the locked configuration, such that the distal bend is immobilized to the lead in the locked configuration; and
    an occluder coupled to the locking member or to the anchoring wire, the occluder being arranged to inhibit a fluid flow in a direction away from the occluder and toward the locking member when the occluder is disposed in a valve annulus;
  whereby the occluder of the cardiac backflow control device can be maintained in position within a valve annulus by cinching the distal bend about the lead and without direct connection to the cardiac tissue.

* * * * *